(12) United States Patent
Zdeblick et al.

(10) Patent No.: US 7,204,798 B2
(45) Date of Patent: Apr. 17, 2007

(54) METHODS AND SYSTEMS FOR MEASURING CARDIAC PARAMETERS

(75) Inventors: Mark Zdeblick, Portola Valley, CA (US); Joseph M. Ruggio, Laguna Hills, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 548 days.

(21) Appl. No.: 10/764,127

(22) Filed: Jan. 23, 2004

(65) Prior Publication Data

US 2004/0254483 A1 Dec. 16, 2004

Related U.S. Application Data

(60) Provisional application No. 60/442,441, filed on Jan. 24, 2003.

(51) Int. Cl.
*A61B 5/02* (2006.01)

(52) U.S. Cl. .................. 600/17; 600/508; 600/587; 600/561; 600/523

(58) Field of Classification Search .................. 600/17, 600/508, 587, 561, 523
See application file for complete search history.

(56) References Cited

U.S. PATENT DOCUMENTS

| | | | |
|---|---|---|---|
| 4,397,314 | A | 8/1983 | Vaguine |
| 4,399,820 | A | 8/1983 | Wirtzfeld et al. |
| 4,603,705 | A | 8/1986 | Speicher et al. |
| 4,628,934 | A | 12/1986 | Pohndorf et al. |
| 4,776,334 | A | 10/1988 | Prionas |
| 4,815,472 | A | 3/1989 | Wise et al. |
| 4,877,032 | A | 10/1989 | Heinze et al. |
| 4,878,898 | A | 11/1989 | Griffin et al. |
| 4,881,410 | A | 11/1989 | Wise et al. |
| 4,902,273 | A | 2/1990 | Choy et al. |

(Continued)

FOREIGN PATENT DOCUMENTS

WO    WO 02/065894 A2    8/2002

(Continued)

OTHER PUBLICATIONS

Paolocci, Nazareno, et al., "Positive inotropic and lusitropic effects of HNO/NO- in falling hearts: Independence from beta-adrenergic signaling", PNAS, vol. 100, No. 9, (Apr. 29, 2003), 5537-5542.*

(Continued)

*Primary Examiner*—Robert Pezzuto
*Assistant Examiner*—Shevon Johnson
(74) *Attorney, Agent, or Firm*—Bret E. Field; Bozicevic, Field & Francis LLP

(57) ABSTRACT

Methods and systems of the present invention provide for measurement of various cardiac parameters. Methods generally involve causing a change in volume and/or pressure in a heart chamber, measuring the change, and calculating at least one cardiac parameter based on the change. Systems typically include at least one actuator, at least one sensor, and a catheter or other device for positioning at least partially in a heart chamber. In some embodiments, the system may also include a controller, such as a computer or other processor, an external actuator, an external sensor, and/or an ECG device. Methods and systems of the invention may be used to more accurately diagnose cardiac conditions in order to make more informed treatment decisions.

77 Claims, 7 Drawing Sheets

U.S. PATENT DOCUMENTS

| | | | |
|---|---|---|---|
| 5,004,275 A | 4/1991 | Miller | |
| 5,035,246 A | 7/1991 | Heuvelmans et al. | |
| 5,072,737 A | 12/1991 | Goulding | |
| 5,113,868 A | 5/1992 | Wise et al. | |
| 5,156,154 A | 10/1992 | Valenta, Jr. et al. | |
| 5,158,536 A * | 10/1992 | Sekins et al. | 604/20 |
| 5,213,098 A | 5/1993 | Bennett et al. | |
| 5,391,199 A | 2/1995 | Ben-Haim | |
| 5,411,532 A | 5/1995 | Mortazavi | |
| 5,411,537 A | 5/1995 | Munshi et al. | |
| 5,417,717 A | 5/1995 | Salo et al. | |
| 5,419,767 A | 5/1995 | Eggers et al. | |
| 5,423,323 A | 6/1995 | Orth | |
| 5,509,411 A | 4/1996 | Littmann et al. | |
| 5,535,752 A | 7/1996 | Halperin et al. | |
| 5,544,656 A | 8/1996 | Pitsillides et al. | |
| 5,549,650 A | 8/1996 | Bornzin et al. | |
| 5,579,764 A | 12/1996 | Goldreyer | |
| 5,591,142 A | 1/1997 | Van Erp | |
| 5,593,430 A | 1/1997 | Renger | |
| 5,662,587 A | 9/1997 | Grundfest et al. | |
| 5,683,429 A | 11/1997 | Mehra | |
| 5,720,768 A | 2/1998 | Verboven-Nelissen | |
| 5,743,267 A | 4/1998 | Nikolic et al. | |
| 5,788,647 A | 8/1998 | Eggers | |
| 5,800,465 A | 9/1998 | Thompson et al. | |
| 5,810,735 A | 9/1998 | Halperin et al. | |
| 5,814,089 A | 9/1998 | Stokes et al. | |
| 5,902,234 A | 5/1999 | Webb | |
| 5,902,248 A | 5/1999 | Millar et al. | |
| 5,913,814 A | 6/1999 | Zantos | |
| 5,924,997 A | 7/1999 | Campbell | |
| 5,935,084 A | 8/1999 | Southworth | |
| 5,999,848 A | 12/1999 | Gord et al. | |
| 6,015,386 A | 1/2000 | Kensey et al. | |
| 6,024,704 A | 2/2000 | Meador et al. | |
| 6,033,398 A | 3/2000 | Farley et al. | |
| 6,038,480 A | 3/2000 | Hrdlicka et al. | |
| 6,078,830 A | 6/2000 | Levin et al. | |
| 6,081,748 A | 6/2000 | Struble et al. | |
| 6,155,267 A | 12/2000 | Nelson | |
| 6,165,135 A | 12/2000 | Neff | |
| 6,171,252 B1 | 1/2001 | Roberts | |
| 6,206,835 B1 | 3/2001 | Spillman, Jr. et al. | |
| 6,206,874 B1 | 3/2001 | Ubby et al. | |
| 6,234,973 B1 | 5/2001 | Meador et al. | |
| 6,264,606 B1 | 7/2001 | Ekwall et al. | |
| 6,277,078 B1 | 8/2001 | Porat et al. | |
| 6,287,256 B1 | 9/2001 | Park et al. | |
| 6,299,582 B1 | 10/2001 | Brockway et al. | |
| 6,301,500 B1 | 10/2001 | Van Herk et al. | |
| 6,309,350 B1 | 10/2001 | Van Tassel et al. | |
| 6,309,385 B1 | 10/2001 | Simpson | |
| 6,328,699 B1 | 12/2001 | Eigler et al. | |
| 6,360,123 B1 | 3/2002 | Kimchi et al. | |
| 6,363,279 B1 | 3/2002 | Ben-Haim et al. | |
| 6,370,431 B1 | 4/2002 | Stoop et al. | |
| 6,418,348 B1 | 7/2002 | Witte | |
| 6,438,408 B1 | 8/2002 | Mulligan et al. | |
| 6,466,820 B1 | 10/2002 | Juran et al. | |
| 6,473,653 B1 | 10/2002 | Schallhorn et al. | |
| 6,477,395 B2 | 11/2002 | Schuman et al. | |
| 6,477,417 B1 | 11/2002 | Levine | |
| 6,496,730 B1 | 12/2002 | Kleckner et al. | |
| 6,580,946 B2 | 6/2003 | Struble | |
| 6,611,714 B1 | 8/2003 | Mo | |
| 6,628,989 B1 | 9/2003 | Penner et al. | |
| 6,666,826 B2 | 12/2003 | Salo et al. | |
| 2001/0047138 A1 | 11/2001 | Kokate et al. | |
| 2001/0053882 A1 | 12/2001 | Haddock et al. | |
| 2002/0026183 A1 | 2/2002 | Simpson | |
| 2002/0045921 A1 | 4/2002 | Wolinsky et al. | |
| 2002/0077568 A1 | 6/2002 | Haddock | |
| 2002/0077673 A1 | 6/2002 | Penner et al. | |
| 2002/0095196 A1 | 7/2002 | Linberg | |
| 2002/0111560 A1 | 8/2002 | Kokate et al. | |
| 2002/0120186 A1 | 8/2002 | Keimel | |
| 2002/0151816 A1 | 10/2002 | Rich et al. | |
| 2002/0156417 A1 | 10/2002 | Rich et al. | |
| 2002/0161307 A1 | 10/2002 | Yu et al. | |
| 2002/0169445 A1 | 11/2002 | Jain et al. | |
| 2003/0153952 A1 | 8/2003 | Auricchio et al. | |
| 2004/0193021 A1 | 9/2004 | Zdeblick | |
| 2004/0215049 A1 | 10/2004 | Zdeblick et al. | |
| 2004/0220637 A1 | 11/2004 | Zdeblick et al. | |

FOREIGN PATENT DOCUMENTS

| | | |
|---|---|---|
| WO | WO 2004/052182 A2 | 6/2004 |
| WO | WO 2004/052182 A3 | 6/2004 |
| WO | WO 2004/066814 A2 | 8/2004 |
| WO | WO 2004/066814 A3 | 8/2004 |
| WO | WO 2004/066817 A2 | 8/2004 |
| WO | WO 2004/066817 A3 | 8/2004 |
| WO | WO 2004/067081 A2 | 8/2004 |
| WO | WO 2004/067081 A3 | 8/2004 |

OTHER PUBLICATIONS

Receveur et al., "Latterally Moving Bi-Stable MEMS DC-Switch for Biomedical Applications," Medtronic Bakken Research Center, The Netherlands (2004), pp. 854-856.

Auricchio et al., "The Pacing Therapies for Congestive Heart Failure (PATH-CHF) Study: Rationate, Design, and Endpoints of a Prospective Randomized Multicenter Study," Am J Cardiol, 1999: 83:130D-135D.

Borky, J.M. and Wise, K.D., "Integrated Signal Conditioning for Silicon Pressure Sensors" *IEEE Transactions on Electron Devices*, vol. ED-26, No. 12 (Dec. 1979) pp. 1906-1910.

Kovacs, "Technology Development For A Chronic Neutral Interface", A dissertation, Stanford University (Aug. 1990), pp. 9, 225-234, 257, 276.

* cited by examiner

METHODS AND SYSTEMS FOR MEASURING CARDIAC PARAMETERS

CROSS REFERENCE TO RELATED APPLICATIONS

The present application claims the priority benefit of U.S. Provisional Patent Application No. 60/442,441, filed Jan. 24, 2003, the full disclosure of which is hereby incorporated by reference. The present application is related to U.S. Patent Application Nos.: 10/764,125; and 10/764,429; both of which are filed concurrently with the present application, and both of which are hereby incorporated fully by reference.

BACKGROUND OF THE INVENTION

1. Field of the Invention

The present invention relates generally to medical devices and methods. More particularly, the present invention relates to medical devices, systems, and methods for determining cardiac performance parameters based on data obtained from an intravascular or intracardiac catheter device.

Intravascular and intraluminal interventions and monitoring have become essential in modem cardiology and other medical fields. Of particular interest to the present invention, a variety of intravascular and intracardiac catheters, implantable sensors, and other devices and systems have been developed for monitoring cardiac performance.

The ability to adequately treat patients suffering from or at risk of cardiovascular diseases can be greatly enhanced by frequent, or real time continuous, monitoring of cardiac performance and function. For example, patients suffering from congestive heart failure could titrate dosages of certain medications if more information were available and information were available more often, relating to cardiac performance and function and how they have responded to drug treatment. Additionally, the need for surgical intervention could also be better assessed if better cardiac performance data were available. For example, it is often difficult to distinguish compromised cardiac valvular function due principally to aortic stenosis or mitral regurgitation from other heart conditions such as myocardial insufficiency that causes reduced pumping ability, especially when moth conditions co-exist.

For these reasons, it would be desirable to provide improved devices, systems, and methods for monitoring cardiac performance and function both in and outside of medical facilities. Such improved devices, systems, and methods should allow for measuring a variety of mechanical, biological, and chemical parameters related to cardiac performance and function and analyzing calculated cardiac performance values based on such measured performance characteristics. Preferably, the devices and apparatus will include one or more intravascular catheters which allow for periodic or continuous collection of in situ cardiac performance data. The systems may then calculate physiodynamic cardiac performance parameters based on the measured internal and external performance data which has been collected. At least some of these objectives will be met by the inventions described hereinafter.

2. Description of the Background Art

Catheters and other intravascular and intracardiac devices for measuring various cardiac, physiological parameters are described in co-pending U.S. patent application Ser. No. 10/734490, entitled "Method and System for Monitoring and Treating Hemodynamic Parameters," filed on Dec. 11, 2003, and commonly assigned with the present application, the full disclosure of which is hereby incorporated by reference. Other catheters and implantable sensors capable of measuring various physiologic parameters in the heart and/or vasculature are described in U.S. Pat. Nos. 5,814,089; 6,328,699 B1; 6,438,408 B1; U.S. Patent Publication Nos. 2001/0053882 A1; 2001/0047138 A1; 2002/0077568 A1; 2002/0111560 A1; 2002/0151816 A1; 2002/0156417; 2002/0169445; and PCT Publication WO 02/065894 A2. The full disclosures of each of these patents and patent publications are incorporated herein by reference.

BRIEF SUMMARY OF THE INVENTION

Methods and systems of the present invention provide for measurement of various cardiac parameters. Methods generally involve causing a change in volume and/or pressure in a heart chamber, measuring the change, and calculating at least one cardiac parameter based on the change. Systems typically include a catheter or other device for positioning at least partially in a heart chamber and including at least one actuator and at least one sensor. A monitoring device such as those described in U.S. patent application Ser. No. 10/734,490, which was previously incorporated by reference, may be used. In some embodiments, an implantable device such as those described in U.S. patent application Ser. No. 60/442,441, which was previously incorporated by reference, may also be used. In some embodiments, the system may also include a controller, such as a computer or other processor, an external actuator, an ECG device, an injector device and/or the like. Methods and systems of the invention may be used to more accurately diagnose cardiac conditions as well as precisely establish disease severity and likely response to therapeutic interventions in order to make patient specific treatment decisions.

In one aspect of the present invention, a method for measuring a cardiac performance parameter includes: causing a change in at least one of volume and pressure in a heart chamber at a selected time during a heart cycle; measuring a change in at least one characteristic of the heart chamber which occurs in response to the volume change and/or the pressure change; and calculating at least one parameter of the heart chamber based on a ratio of the measured change in the characteristic to either the volume change or the pressure change. Similar measurements of various hemodynamic parameters may be made after changes induced by alterations in heart rate, electrochemical coupling, electrophysiological timing, and peripheral vascular changes.

In some embodiments, causing the change involves introducing a volume of fluid into the heart chamber during diastole. The fluid may be constrained or unconstrained. For example, introducing the volume of fluid may involve releasing the fluid within the heart chamber via one or more apertures in a catheter positioned in the chamber. More specifically, introducing the volume of fluid may involve inflating an expandable balloon coupled with a catheter positioned in the heart chamber. For example, inflating the balloon may involve inflating the balloon during systole of the heart and deflating the balloon during diastole of the heart immediately following the systole. Alternatively, introducing the volume of fluid involves: inflating a balloon within the heart chamber during systole; deflating the balloon during diastole immediately following the systole; and releasing an amount of unconstrained fluid within the heart chamber during the diastole. For example, the balloon may be deflated by a volume equal to the amount of the released fluid. Alternatively, the balloon may be deflated by a volume greater than the amount of the released fluid. In some embodiments, causing the change comprises activating a hydrophone at least once during diastole. The hydrophone may be activated at any suitable frequency, but in some embodiments it is activated at a frequency of about 200 Hz. Further embodiments involve changes in diastolic filling period and post-extrasystolic potentiation related measurements, as occurs with spontaneously or exogenously induced paroxysmal ventricular tachycardia ("PVCs"). Still other embodiments involve measuring changes induced by exercise, alteration in heart rate and loading or unloading conditions, and predicting response to electrophysiological or pharmacological stimuli or interventions.

Optionally, a method may further include measuring the heart cycle using an electrocardiogram device, with the selected time during the heart cycle being selected using the electrocardiogram measurement. In another embodiment, the method may comprise measuring the heart cycle using at least one sensor on a catheter positioned in the heart chamber, wherein the selected time during the heart cycle is selected using the sensor measurement. The timing of various steps may be different in different embodiments. For example, in one embodiment, the measuring step is performed immediately after causing a change in at least one of volume and pressure. In another embodiment, the measuring step is performed during at least a portion of the heart cycle after the change in at least one of the volume and pressure. Optionally, the method may further comprise causing a change, measuring and calculating steps over a series of two or more consecutive heart cycles.

In one embodiment, measuring the change comprises measuring a change in at least one pressure within the heart chamber. For example, measuring the change in pressure may involve measuring a change in end-diastolic pressure and a change in end-systolic pressure. In such embodiments, calculating the at least one parameter may involve calculating a cardiac pressure reserve, comprising: calculating a first difference between a first end-systolic pressure and a second end-systolic pressure; calculating a second difference between a first end-diastolic pressure and a second end-diastolic pressure; and dividing the first difference by the second difference. The method may optionally further include providing at least one of the end-diastolic pressures, the end-systolic pressures and the cardiac pressure reserve for display on a display device. For example, the providing step may involve providing data in the form of a plot, with at least one end-diastolic pressure on one axis of the plot and at least one end-systolic pressure on a perpendicular axis of the plot. Characteristics and parameters may be measured and calculated in any heart chamber, but in one embodiment, measuring the change comprises measuring a change in left ventricular end-diastolic pressure and a change in left ventricular end-systolic pressure.

In another embodiment, measuring the change involves measuring a change in at least one volume within the heart chamber. For example, measuring the change may include measuring a change in end-diastolic volume and a change in end-systolic volume. In some embodiments, calculating the parameter comprises calculating a volume reserve, which involves: calculating a first difference between a first end-systolic volume and a second end-systolic volume; calculating a second difference between a first end-diastolic volume and a second end-diastolic volume; and dividing the first difference by the second difference. The method may optionally further include providing at least one of the end-diastolic volumes, the end-systolic volumes and the volume reserve for display on a display device. For example, the providing step may involve providing data in the form of a plot, with at least one end-diastolic volume on one axis of the plot and at least one end-systolic volume on a perpendicular axis of the plot. Measuring the change, in some embodiments, involves measuring a change in a left ventricular end-diastolic volume and a change in a left ventricular end-systolic volume.

In some embodiments, measuring the change comprises measuring a change in at least one pressure and a change in at least one volume within the heart chamber. Measuring the change, for example, may involve measuring a change in end-diastolic volume and a change in end-diastolic pressure. The end-diastolic moment may be determined using the volume sensor, as ventricular volume is at a maximum at end-diastole. In this embodiment, the method may further include providing pressure and volume data as a plot, with at least one volume on one axis of the plot and at least one volume on a perpendicular axis of the plot. Calculating the at least one parameter may involve calculating a lusitropic stiffness of the heart chamber, which involves: calculating a first difference between a second end-diastolic pressure and a first end-diastolic pressure; calculating a second difference between a second end-diastolic volume and a first end-diastolic volume; and dividing the first difference by the second difference. The method may further involve providing at least one of the volumes, the pressures and the lusitropic stiffness for display on a display device. In another embodiment, calculating the at least one parameter comprises calculating a lusitropic compliance of the heart chamber, which involves: calculating a first difference between a second end-diastolic volume and a first end-diastolic volume; calculating a second difference between a second end-diastolic pressure and a first end-diastolic pressure; and dividing the first difference by the second difference. In various embodiments, methods may further include providing at least one of the volumes, the pressures and the lusitropic compliance for display on a display device. In some embodiments, measurements may be taken during isovolumetric relaxation and isovolumetric contraction.

In yet another embodiment, measuring the change comprises measuring a change in end-systolic volume and a change in end-systolic pressure. The end-systolic moment may be determined using the volume sensor, as ventricular volume is at a minimum at end-systole. Some embodiments may further comprise providing volume and pressure data as a plot, with at least one volume on one axis of the plot and at least one pressure on a perpendicular axis of the plot. Calculating the at least one parameter, in one embodiment, comprises calculating an inotropic stiffness of the heart chamber, which involves: calculating a first difference between a second end-systolic pressure and a first end-systolic pressure; calculating a second difference between a second end-systolic volume and a first end-systolic volume; and dividing the first difference by the second difference. This method may also include providing at least one of the volumes, the pressures and the inotropic stiffness for display on a display device.

In another embodiment, calculating the at least one parameter comprises calculating an inotropic compliance of the heart chamber, which includes: calculating a first difference between a second end-systolic volume and a first end-systolic volume; calculating a second difference between a second end-systolic pressure and a first end-systolic pressure; and dividing the first difference by the second difference. Again, any of the volumes, the pressures and the inotropic compliance may be provided for display on a display device.

In another embodiment, the measuring and calculating steps include: continuously measuring a pressure and volume in the heart chamber during at least two heart cycles, a first of the heart cycles occurring before the change-causing step; calculating a first integral of the product of the pressure and the volume as the volume increases due to the change-causing step; calculating a second integral of the product of the pressure and the volume as the volume decreases; and calculating a myocardial work of the heart chamber by subtracting the second integral from the first integral. Optionally, this method may further include: calculating a first myocardial work for the first heart cycle; calculating a second myocardial work for a second heart cycle; measuring a first end-diastolic pressure for the first heart cycle and a second end-diastolic pressure for the second heart cycle; and calculating a myocardial reserve by dividing a difference between the second and first myocardial works by a difference between the second and the first end-diastolic pressures. Such a method may further include: calculating a body surface area; and calculating a myocardial reserve index by dividing the myocardial reserve by the body surface area. Myocardial work may be calculated for a left ventricle of a heart, the right ventricle of a heart, or any other chamber.

In yet another embodiment, a method as described above may further include: measuring a change in at least one flow rate of blood flowing out of the heart chamber which occurs in response to the volume and/or pressure change; and calculating at least one flow-related parameter of the heart chamber based on a ratio of the measured change in the flow rate to the volume and/or pressure change. In such embodiments, measuring the change in the flow rate may involve measuring at least one flow rate in an aorta. Alternatively, measuring the change in the flow rate may involve measuring at least one flow rate in at least one pulmonary artery.

In one embodiment, calculating the flow-related parameter comprises calculating at least one stroke volume of a heart from which the flow rate is measured, and the method further includes: estimating a first cardiac output for the heart; measuring a pulse rate of the heart; calculating a first stroke volume by dividing the first cardiac output by the heart rate; calculating a first integral of the flow rate over a number of heart cycles; calculating a second stroke volume by dividing the first integral by the number of heart cycles; calculating a scaling factor by dividing the first stroke volume by the second stroke volume; calculating a selected integral of the flow rate during a selected heart cycle; and calculating the selected stroke volume by multiplying the selected integral by the scaling factor. In some embodiments, the first cardiac output is estimated using at least one of Fick's method and a dilution method. In some embodiments, the method further includes determining a selected cardiac output by dividing the selected stroke volume by a time of duration of the selected heart cycle. The purpose of this calibration procedure is to allow the catheter system to measure the stroke volume and effective cardiac output of each heart cycle. Current methods of Fick or dilution average the cardiac output over many heart cycles. Such embodiments may additionally involve, for example measuring a body surface area, and calculating a cardiac index by dividing the selected cardiac output by the body surface area.

Some embodiments further include: determining a first selected cardiac output and a second selected cardiac output for first and second heart cycles; measuring first end-diastolic pressure and a second end-diastolic pressure for the first and second heart cycles; and calculating a cardiac reserve by dividing a difference between the second and first selected cardiac outputs by a difference between the second and first end-diastolic pressures. For example, the method may further involve: measuring a body surface area, and calculating a cardiac reserve index by dividing the calculated cardiac reserve by the body surface area.

In one embodiment, the method further comprises: calculating a first stroke volume and a second stroke volume for first and second cardiac cycles; measuring first end-diastolic pressure and a second end-diastolic pressure for the first and second heart cycles; and calculating a stroke reserve by dividing a difference between the second and first calculated stroke volumes by a difference between the second and first end-diastolic pressures. This method may further include: measuring a body surface area; and calculating a stroke volume reserve index by dividing the calculated stroke volume reserve by the body surface area. Optionally, it may further comprise: measuring an average systolic pressure in at least one outflow artery adjacent the heart; measuring an average diastolic pressure in the heart chamber; calculating a difference between the average systolic pressure and the average diastolic pressure; and calculating a stroke work by multiplying the difference by the stroke volume.

In some embodiments, the method further comprises: calculating a first stroke work and a second stroke work for first and second cardiac cycles; measuring first end-diastolic pressure and a second end-diastolic pressure for the first and second heart cycles; and calculating a stroke work reserve by dividing a difference between the second and first calculated stroke works by a difference between the second and first end-diastolic pressures. Optionally, the method may further include: measuring a body surface area; and calculating a stroke work reserve index by dividing the calculated stroke work reserve by the body surface area. The method may also optionally include measuring post-systolic potentiation and its ability to estimate myocardial reserve.

In the above embodiments, the at least one outflow artery may be an aorta, at least one pulmonary artery, or any other suitable outflow artery. The above embodiments may optionally further involve calculating a cardiac efficiency by dividing the stroke work by the myocardial work.

In one embodiment, a method includes: calculating a first stroke volume and a second stroke volume for first and second cardiac cycles; measuring first end-diastolic volume and a second end-diastolic volume for the first and second heart cycles; and calculating a cardiac amplification by dividing a difference between the second and first calculated stroke volumes by a difference between the second and first end-diastolic volumes.

In another aspect of the invention, a system for measuring one or more parameters of a heart includes: a catheter comprising at least one sensor and at least one expandable element, usually comprising an actuator for introducing a known volume of constrained or unconstrained fluid into at least one chamber of the heart at a selected time during a heart cycle to effect a volume change in the heart chamber; a fluid source coupled with the catheter for providing fluid to the actuator; and a processor coupled with the catheter for processing data sensed by the at least two sensors. In some embodiments, the sensor may include at least one of a pressure sensor and a volume sensor. Optionally, the sensor may further comprises at least one of a flow sensor for measuring blood flowing from the heart and a vascular pressure sensor for measuring pressure in a vessel extending from the heart. Alternatively, the catheter could comprise a means for deforming a heart chamber, such as a pusher for outwardly deflecting or otherwise mechanically reshaping the heart chamber to induce a change in pressure or change in volume. In one embodiment, a flow meter may be included to measure distensibilty characteristics of a heart chamber.

In some embodiments, the flow sensor or pressure sensor is disposed in a location to measure flow or pressure in at least one of an aorta and a pulmonary artery. In some embodiments, at least one sensor comprises a hydrophone. In some embodiments, the sensor comprises at least one ultrasound transducer for measuring a distance within a chamber of the heart. In some embodiments, for example, the ultrasound transducer comprises: a first pair of ultrasound transducers coupled with the catheter in parallel with a longitudinal axis of the catheter for measuring a first distance between the transducers and the wall of the heart chamber; a second pair of ultrasound transducers coupled with the catheter in an orientation 90-degrees rotated from the first pair of transducers for measuring second and third distances to a wall of the heart chamber; and a third pair of ultrasound transducers coupled with the catheter in an orientation 90-degrees rotated from the first and second pairs of transducers for measuring fourth and fifth distances to a wall of the heart chamber.

Any actuator may be suitable for use in the system. For example, an actuator may comprise at least one of a fluid outlet port and an expandable balloon, the expandable balloon being expandable by introducing the fluid into the balloon. In some embodiments, the system further includes an electrocardiogram device coupled with the processor for measuring the heart cycle

DETAILED DESCRIPTION OF THE INVENTION

The present invention is directed at methods, systems, and apparatus for monitoring one or more patient parameters, particularly cardiac performance parameters. The apparatus of the present invention typically includes a catheter having one or more sensors and one or more actuators. One such catheter, for example, is described in U.S. patent application Ser. No. 10/734,490, entitled "Method and System for Monitoring and Treating Hemodynamic Parameters," previously incorporated by reference. Systems of the present invention typically include a catheter, an external actuation device, and a controller. In some embodiments, systems may also include an electrocardiogram (ECG) device, other similar heart monitoring device(s), thermistors, cardiac output measuring consoles, injector devices, phonocardiography devices or the like for use in conjunction with the catheter. Additionally, some embodiments may employ one or more implantable devices, such as those described in A monitoring device such as those described in U.S. patent application Ser. No. 10/734,490, entitled "Method and System for Remote Hemodynamic Monitoring," which was previously incorporated by reference. Methods of the present invention generally involve causing a change in a characteristic of a heart, measuring the change, and calculating a cardiac parameter based on the change.

Figure 1:
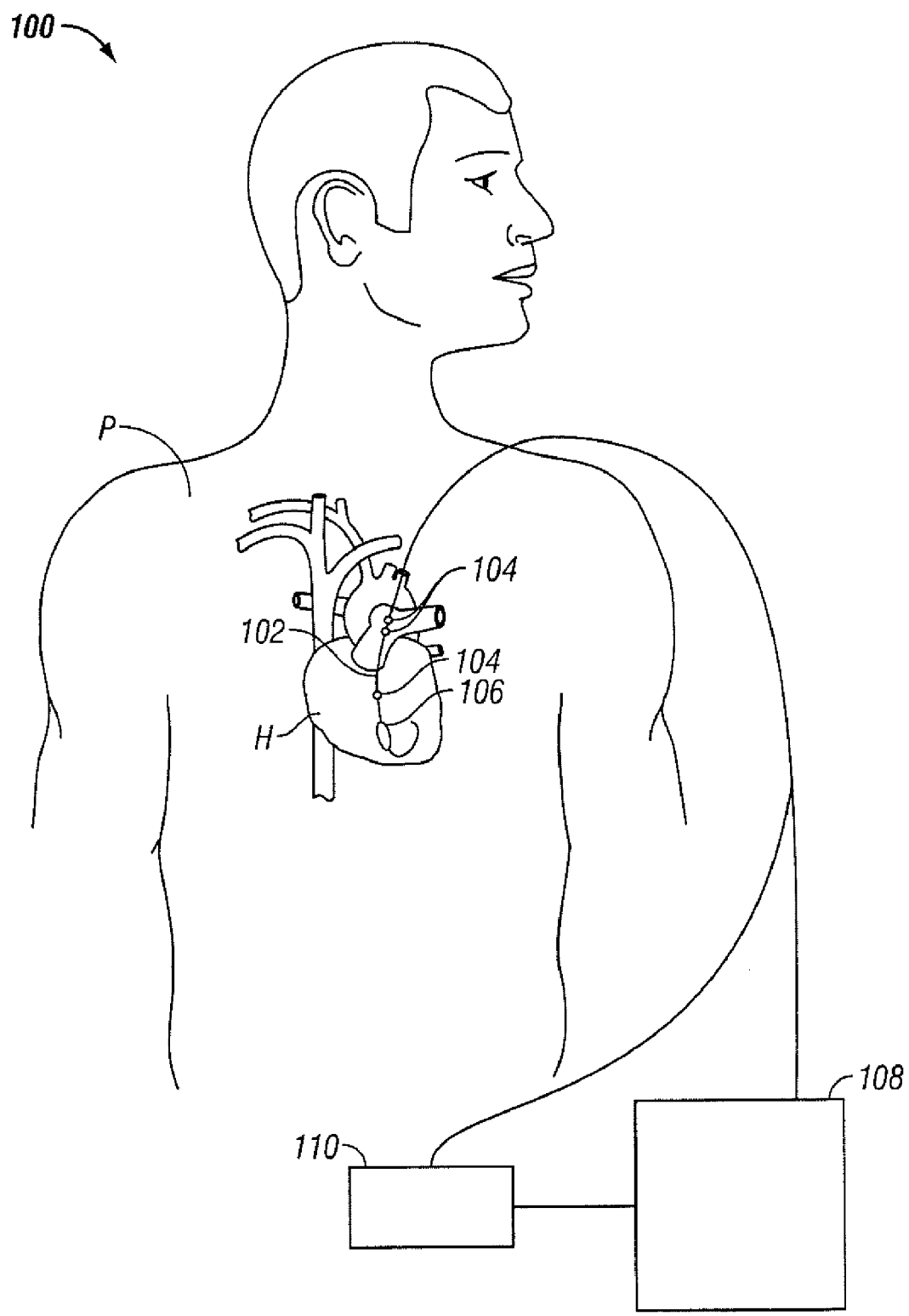
FIG. 1 illustrates a catheter-based cardiac performance monitoring system in accordance with the principles of the present invention.

Referring now to FIG. 1, an exemplary system 100 constructed in accordance with the principles of the present invention comprises a catheter device 102 placed in a heart H of a patient P, a controller 108 coupled with catheter device 102, and an external actuator 110 coupled with controller 108 and catheter device 102. As will be described further below, catheter device 102 typically includes one or more sensors 104 and one or more actuators 106 and can be placed in any suitable location in the heart H or vasculature. Sensors 104 may be adapted to measure a variety of physiological parameters characteristic of heart function, while actuators 106 may be adapted to effect a change within a chamber, multiple chambers, or other areas in or around the heart H. Controller 108 typically receives data from sensors 104 and also activates various components of catheter 102, as well as external actuator 110. Controller 108 may also receive data from other various components, such as an ECG device. External actuator 110 generally activates one or more actuators 106 on catheter 102, via instructions from controller 108.

Systems according to the present invention may take a variety of specific forms, including both specialized and off-the-shelf equipment. Components shown in FIG. 1 may be combined and/or additional components may be added to system 100. Usually, the catheter device 102 will be specially fabricated in accordance with the principles of the present invention, although it may be possible, in some instances, to employ more conventional sensor devices which may be commercially acquired now or in the future. Furthermore, the external controller 108 or external actuator 110 may at least partly comprise commercially available equipment. Often, general purpose computers and workstations may be programmed to perform many of the functions and calculations of the systems and methods of the present inventions.

Figure 2:
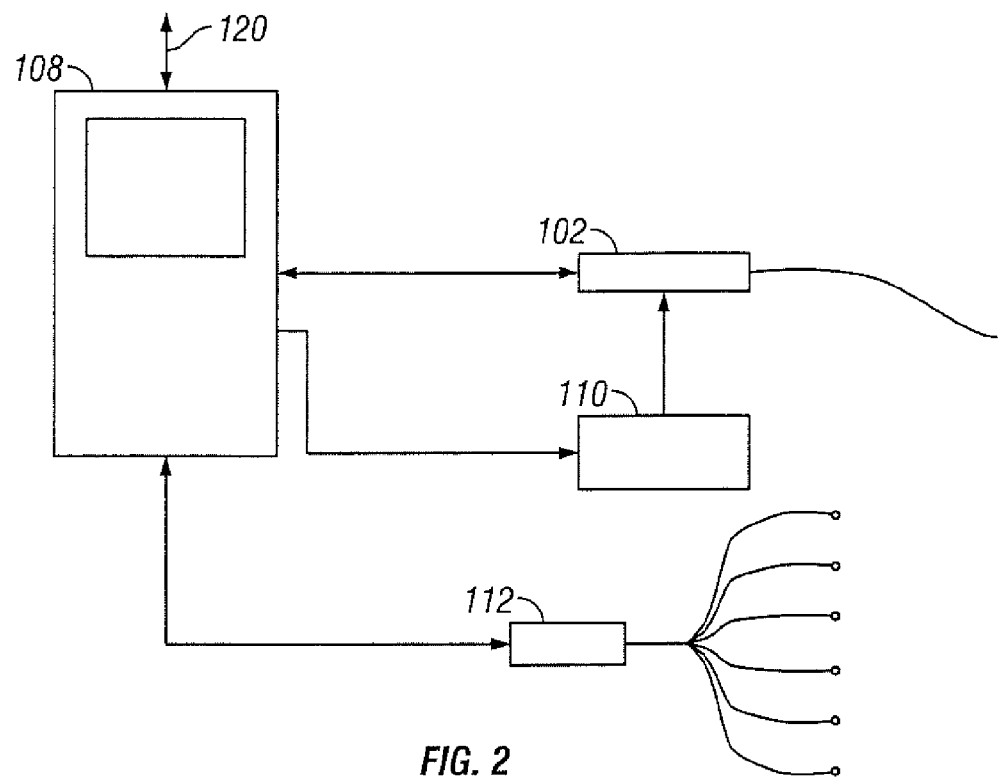
FIG. 2 is a schematic illustration of the system according to FIG. 1, including interfaces between various components of the system.

Referring now to FIG. 2, the various components of system 100 illustrated in FIG. 1, as well as an ECG device 210, are shown with arrows designating directions in which data may flow between components of system 100 in some embodiments. For example, data may flow from controller 108 to catheter 102, such as data activating one or more sensors, energy may be transmitted from controller 108 to catheter 102 and the like. Catheter 102 may, in turn, transmit sensed data to controller 108. External actuator 110 may receive data from controller 108, telling it when to activate one or more actuators on catheter 102. An ECG device 112 may be activated by controller 108 and may provide cardiac data to controller 108 which may be used by controller 108 to operate other components of system 100. Generally, any suitable connectivity and transmission of data, energy, and the like between any suitable components of system 100 is contemplated within the scope of the present invention.

The external controller 108 may provide direct user input/output capabilities, i.e., including screens, printer interfaces, read/write data storage capabilities, etc. Optionally, the external controller 108 may require interface with a further computer, workstation, or other device which interfaces directly with the user and provides the input/output capabilities. In all cases, the external controller 108 may provide data input/output connections shown schematically as line 120.

Figure 3:
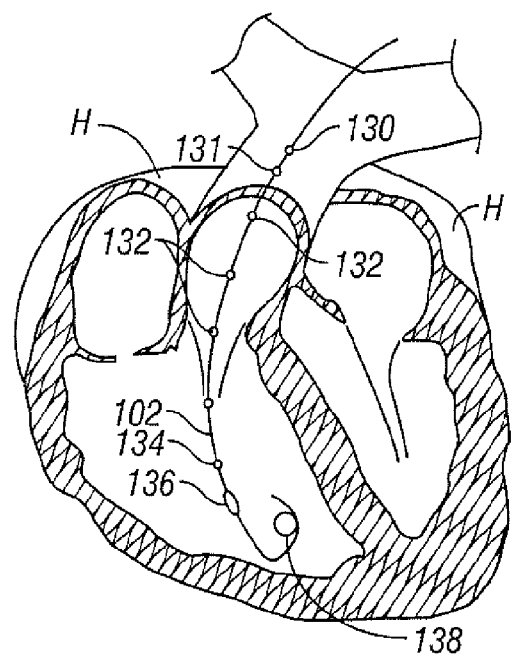
FIG. 3 illustrates a patient's heart with a catheter in place, having multiple sensors and an actuator, according to one embodiment of the present invention.

Referring now to FIG. 3, catheter 102 for placement in a heart H may take a variety of forms. Again, for further description of an exemplary catheter which may be used in the methods of the present invention, reference may be made to U.S. patent application Ser. No. 10/734,490, entitled "Method and System for Monitoring and Treating Hemodynamic Parameters," previously incorporated by reference. In other embodiments, other catheters may be used and/or multiple catheters may be used simultaneously or in conjunction. Catheter 102 may be placed in any suitable location. In FIG. 3, catheter 102 is shown descending through the aorta into the left ventricle of the heart H, with sensors both in the aorta and in the left ventricle. Alternatively, catheter could be placed in the right side of the heart, sensors could be positioned in multiple heart chambers, actuators could be placed in the aorta, pulmonary artery, or inferior vena cava, and/or the like. Thus, although catheter 102 is shown in the left ventricle and is often described below in terms of measuring left ventricular function, catheter 102 and system 100 of the present invention may be placed in any suitable portion of the heart and/or structures surrounding the heart.

Catheter 102 may generally include any suitable combination of sensors and actuators, and the sensors and actuators may be disposed along catheter 102 at any desired locations. In FIG. 3, for example, sensors include a flow sensor 130, an electrical conductivity sensor 131, multiple pressure sensors 132 aligned in a linear array, an ultrasound sensor 134 comprising a rotated cube having multiple ultrasound transducers, and a hydrophone 138. Also included on catheter is an actuator, which may comprise a volume actuator, pressure actuator or the like. Volume actuators may include one or more fluid injection ports, one or more fluid aspiration ports, an inflatable balloon, a combination thereof, and/or the like. Some embodiments may also include one or more thermistors.

Methods of the present invention generally involve inducing a change in a characteristic of a heart or heart chamber, measuring the change, and calculating a parameter that changes due to the measured change. Oftentimes, the changed characteristic will be either pressure, volume, or both, and the change will typically be induced by one or more actuators on the catheter. Of course, multiple changes and/or other types of changes may be induced and measured, and multiple parameters may be calculated in any given procedure or method. Such other types of changed characteristics may include but are not limited to changes in flow, oxygen content, content of any other suitable gas such as carbon dioxide, dimensions of a chamber or wall thickness or the like, temperature, and the like. The calculated parameter (or parameters) will often provide valuable diagnostic information regarding a patient's heart function and performance, to allow a physician to make accurate diagnoses and patient specific treatment decisions, such as whether to treat a patient pharmaceutically, with device intervention, with surgery, or with none or some combination thereof.

In some embodiments, the catheter system is used to measure various properties of the heart throughout a cardiac cycle, changing the volume and pressure of a cardiac chamber using actuation means, and measuring the immediate and cyclical responses to this change. Some myocardial properties are described by the response at a single point in time to the actuation means: the ratio of the change of one parameter over the change of some other parameter induced by the actuation means. Ventricular compliance, for example, is the immediate change in ventricular pressure induced by a change in ventricular volume. Aortic valvular gradient reserve, a further example, is the change in the maximum aortic trans-valvular pressure gradient measured at the point of maximum aortic flow, the change of which results from a modified LVEDP. Other cardiac properties are described by the cyclical output of the heart following two different "initial" conditions. In this context, "initial conditions" is defined as those conditions that exist in the ventricle (or other heart chamber) at End Diastole, the point in time when the ventricle begins to contract. Cardiac Reserve, for example, is the increase in cardiac output induced by an increase in LVEDP. Similarly, methods of the present invention may be used to derive the "reserve" of a number of cardiac properties. In this context, "reserve" describes the change in a property due to a change in the inducing conditions.

For example, in one embodiment a catheter may be used to measure in real-time the pressure and volume of the left ventricle. The catheter may also be capable of measuring in real-time the blood flow rate through the aorta. From these measurements the catheter system can calculate the left ventricular end-diastolic pressure (LVEDP), left ventricular end-diastolic volume LVEDV, left ventricular end-systolic pressure LVESP, left ventricular end-diastolic volume LVESV, cycle time (heart rate), change in pressure divided by change in time (dP/dt), regurgitation in the aortic and mitral valves, and/or the ejection fraction of the heart for each cycle. Based on the data sensed by the catheter, the system may also calculate, display and record the Pressure-Volume loop of the left ventricle. An optional right catheter, when used, allows simultaneous measurements of the right atrial and/or right-sided ventricular pressure. With these measurements, the system may be used to determine the pulmonary vascular resistance (PVR) and the systemic vascular resistance (SVR) for each cycle.

Methods of the present invention also typically involve effecting a change in the volume or pressure in a heart chamber. By effecting such a change and measuring the change, various cardiac parameters may be measured in furtherance of accurate cardiac diagnosis and characterization. In one embodiment, the catheter is used to add fluid to the ventricle during diastole to increase end diastolic pressure and volume. Alternatively or additionally, a balloon placed in the ventricle may be inflated or deflated during diastole to adjust the end-diastolic pressure and volume. In another embodiment, a hydrophone transmitter may be used to alter volume in a heart chamber. An actuator such as a hydrophone may be used to effect volume changes at a rapid rate, such as 100 or more times per second. In still other embodiments, the afterload of a heart may be modified, either in addition to one of the methods described above or alone. For example, an inflatable balloon positioned in the aorta may be inflated to increase afterload. Similarly, preload may be modified, using apparatus such as an inflatable balloon positioned in the inferior vena cava or right atrium. Finally, the initial conditions of the heart may be modified pharmaceutically by injecting various agents into the blood stream or by exercising the patient through, for example, lifting saline bags or by generating Preventricular Contractions, (PVC's) which in general have a lower than usual end diastolic volume and the cycle immediately following PVC's, which in general have a higher than usual end-diastolic volume and more vigorous contraction. This latter method, cardiac response to a PVC, illustrates the value of the ability to measure stroke volume on a per-cycle basis. The many suitable methods may be used to effect a volume and/or pressure change in one or more chambers of a heart, in order to arrive at useful cardiac parameter data.

By effecting a change in volume or pressure in a heart chamber, measuring the change in a parameter that is effected by the change, and calculating a parameter based on the change, methods of the present invention may be used to derive novel parameters that may be used to help characterize a patient's heart in quantitative terms. By calculating a ratio of the increase in stroke volume over the increase in end-diastolic pressure, for example, the system calculates a measure of cardiac reserve. In another example, a parameter called cardiac amplification may be measured as the ratio of the increase in stroke volume to the increase in end-diastolic volume. In yet another example, continuous measurement of compliance may be obtained by calculating the ratio of change in pressure caused by a change in volume.

As discussed above, any suitable combination of sensors may be disposed along a catheter of the present invention to measure any of a number of suitable cardiac parameters. For example, absolute pressure may be measured by one or more sensors. Such pressure sensors, for example, may have a frequency response of at least 100 Hz in some embodiments. In one embodiment, at least one pressure sensor is located near the distal end of the catheter, a second pressure sensor is located on the catheter to allow the sensor to be positioned just proximal to the aortic valve (when the catheter is positioned in the left ventricle), and a third pressure sensor is located outside the body of the patient to detect atmospheric pressure. In other embodiments, the third, atmospheric sensor may be eliminated, atmospheric pressure may be alternatively measured on the external computation device (the interface "box"), additional sensors may be added, positions of sensors may be changed, and/or the like. In some embodiments, for example, one or more sensors may be used to measure transthoracic pressure, which changes when breathing, which is particularly important when diagnosing tamponade, or to measure a finer spatial pressure gradient across the aortic valve and into the left ventricle, which is particularly important when differentially diagnosing aortic stenosis (AS) and hypertrophic obstructive cardiomyopathy (HOCM) as well as hypertrophic non-obstructive cardiomyopathy (HNOCM).

Volume measurement in a heart chamber such as the left ventricle may be accomplished by any of a variety of sensors and methods. In one embodiment, a sensor comprising six ultrasound transducers mounted orthogonal to each other is used to measure six orthogonal radii of curvature of an assumed ovoid shape of the heart. These measurements may be used to determine multiple estimates of the ventricular volume at any suitable interval, such as once every heart cycle or even multiple times per second. An alternative embodiment uses a phased array ultrasonic system to measure the cross-sectional area of a heart chamber at multiple points along it's axis throughout a heart cycle to compute a measurement of volume using Taylor's theorem. Yet another embodiment employs the release of a known amount of dye or electrically conductive liquid, whose concentration is then measured to estimate the volume of blood into which it was diluted. A further method involves the measurement of the conductivity of the blood in the ventricle, commonly referred to as conductance plethysmography.

Catheters and systems of the invention can be used to calculate cardiac output, which may be averaged over a number of cycles. Such calculations may be made using any suitable method, such as thermal dilution, dye dilution, conduction dilution, or Fick's method using oxygen consumption.

Another parameter which may be measured is blood velocity, such as blood velocity in the aorta or in one or more pulmonary arteries. Any suitable measurement method may be used, including thermal dilution, shear force measurement, a pitot-tube method (stagnant v. dynamic flow), Doppler ultrasound, or any other suitable methods, including methods not yet discovered. By integrating blood velocity throughout a cardiac cycle, the system may be used to derive a stroke volume for each cycle. Stroke volume per cycle may then be used, with measured heart rate, to calculate per-cycle cardiac output. This per-cycle value of cardiac output may be calibrated using the cardiac output measuring system.

In many embodiments, a catheter has the ability to modify the volume and/or pressure in a heart chamber by introducing and/or removing fluid via actuator 106. In some embodiments, fluid may be introduced and/or removed during diastole to change the end diastolic pressure and/or volume. In other embodiments, actuator 106 may rapidly expand or contract or introduce and remove the same amount repeatedly during an entire cycle of the heart. In some embodiments, such rapid introductions/removals may occur at a rate of greater than 100 Hz but less than 1000 Hz, although other rates are contemplated within the scope of the invention. In one embodiment, external volume actuator 110, such as a pump, is coupled with catheter 102 to perform the introduction and/or removal functions. Alternatively, external actuator 110 may perform introduction or withdrawal of large quantities of fluid to alter cardiac output, while actuator 106 on the catheter performs a higher frequency modulation.

As is discussed above, various embodiments of devices and methods of the present invention may include any suitable combination of one or more actuator and one or more sensor. For example, a catheter that includes one pressure sensor 104 and one actuator 106, the latter coupled to an external actuator 110, may be used to measure at least an increase in left ventricular end-systolic pressure with increasing left ventricular end-diastolic pressure. This measurement provides one means for characterizing cardiac reserve, referred to above as pressure reserve. Thus, the preceding and following descriptions of specific systems, devices, and/or methods for measuring and calculating cardiac parameters should not be interpreted to limit the scope of the invention in any way, but are provided for exemplary purposes only.

Actuator 106 may be used to modify the pressure and/or volume in a heart chamber at one or more precise times during a cardiac cycle. In one embodiment, actuator 106 provides such modifications by delivering a fluid (gas or liquid) into or out of the chamber. Delivery may comprise direct delivery of fluid into the chamber, such as through one or more apertures in actuator 106. Alternatively, fluid may be introduced via an inflatable balloon or similar structure. The timing of fluid deliveries and/or withdrawals may be coordinated by controller 108, which may use data from one or more sensors 104, an optional ECG system 112, and/or the like. The controller 108 may also perform other digital signal processing, memory, and display functions. A display may be used to present one or more novel parameters to a doctor or other user, including but not limited to the various property and reserve parameters described below.

In addition to many known cardiac parameters, such as cardiac output and ventricular pressure, catheter devices and methods of the present invention provide for measurement of additional parameters that have not been previously measured. A table (Table 1) summarizing some of these is presented below. Others parameters may also be measured or calculated, such as the inverse of a parameter or the use of the parameter for a specific chamber or valve. Thus, the following table is not exhaustive.

TABLE 1

| Name | Variable | Equation | Description |
| --- | --- | --- | --- |
| Left Ventricle Pressure | LVP | Measured directly | Gauge pressure in Left Ventricle |
| Left Ventricular Volume | LVV | Measured directly | Volume of left ventricle |
| End diastolic volume | EDV | Measured directly | Volume of chamber when volume is maximum |
| End systolic volume | ESV | Measured directly | Volume of chamber when volume is minimum |
| End diastolic pressure | EDP | Direct measurement | Gauge Pressure in chamber when volume is maximum |
| End systolic pressure | ESP | Direct measurement | Gauge Pressure in chamber when volume is minimum |
| Aortic Pressure | AOP | Direct measurement | Gauge Pressure in aorta just distal to Aortic Valve |
| Ejection Fraction | EF | (EDV − ESV)/EDV | Describes the percentage of blood ejected from chamber (usually LV) during a cycle |
| Cardiac Output | CO | Fick or dilution or k * ∫Velocity * HR | Total amount of blood pumped by the heart per minute |
| Cardiac Index | CI | CO/BSA | Cardiac output normalize by Body Surface Area |
| Stroke Volume | SV | CO/HR or k * ∫Velocity | Net amount of blood ejected into aorta in one cycle. Measured either from cardiac output or from the integral of calibrated blood velocity during a cycle. |
| Stroke Volume Index | SVI | SV/BSA | Stroke volume normalize by Body Surface Area |
| Pressure Reserve | PR | d(LVESP)/d(LVEDP) | Marginal change in end systolic pressure due to a marginal change in end-diastolic pressure |
| Volume Reserve | VR | d(LVESV)/d(LVEDV) | Marginal change in end systolic volume due to a marginal change in end-diastolic volume |
| Cardiac Reserve | CR | d(CO)/d(LVEDP) | Marginal increase in cardiac output due to a marginal increase in LVEDP |
| Cardiac Reserve Index | CRI | d(CI)/d(LVEDP) | Cardiac Reserve normalized by Body Surface Area |
| Stroke Reserve | SR | d(SV)/d(LVEDP) | Marginal increase in stroke volume due to a marginal increase in LVEDP |
| Stroke Reserve Index | SRI | d(SVI)/d(LVEDP) | Stroke Reserve normalized by Body Surface Area |
| Myocardial Work | MyW | $\int_{dV/dt<0} P dv - \int_{dV/dt>0} P dv$ | Work performed by myocardial tissue during a single cycle |

TABLE 1-continued

| Name | Variable | Equation | Description |
|---|---|---|---|
| Left Ventricle Pressure | LVP | Measured directly | Gauge pressure in Left |
| Myocardial Work Moment | MyWM | $\int_{dV/dt<0} PV\,dv - \int_{dV/dt>0} PV\,dv$ | Work moment performed by myocardial tissue during a single cycle |
| Myocardial Work Index | MyWI | MW/BSA | Myocardial work normalized by Body Surface Area |
| Myocardial Reserve | $M_yR$ | d(MW)/d(LVEDP) | Marginal increase myocardial reserve due to a marginal increase in LVEDP |
| Myocardial Reserve Index | $M_yRI$ | d(MWI)/d(LVEDP) | Myocardial Reserve normalized by Body Surface Area |
| Stroke Work | SW | $SV * (\overline{AOP_{Systole}} - \overline{LVP_{Diastole}})$ | Hemodynamic work performed by the left ventricle during a single cycle |
| Stroke Work Index | SWI | SW/BSA | Stroke Work normalized by Body Surface Area |
| Stroke Work Reserve | SWR | d(SW)/d(LVEDP) | Marginal increase in Stroke Work due to a marginal increase in LVEDP |
| Stroke Work Reserve Index | SWRI | SWR/BSA | Stroke Work Reserve normalized by Body Surface Area |
| Systolic Ejection Period | SEP | Direct measurement | Time during which blood is ejected from LV into Aorta |
| Stroke Power | SP | SW/SEP | Power performed by heart against circulatory system |
| Stroke Power Index | SPI | SP/BSA | Stroke Power normalized by Body Surface Area |
| Stroke Power Reserve | SPR | d(SP)/d(LVEDP) | Marginal increase Stroke Power due to a marginal increase in LVEDP |
| Stroke Power Reserve Index surface areas | SPRI | SPR/BSA | Stroke Power Reserve normalized by body |
| Myocardial Power | MyP | MyW/SEP | Power performed by the myocardia during systole |
| Myocardial Power Index | MyPI | MyP/BSA surface area | Myocardial Power normalized by body |
| Myocardial Power Reserve | MyPR | d(MyP)/d(LVEDP) | Marginal increase in myocardial power due to a marginal increase in end diastolic pressure |
| Myocardial Power Reserve Index | MyPRI | MyPR/BSA | Myocardial Power reserve normalized by body surface area |
| Myocardial Power Requirement | MyPSV | MyP/SV | Power required to deliver unit stroke volume |
| Ejection contractility | EC | $\dfrac{P_2V_2 - P_1V_1}{(t_2 - t_1)\int_{t_1}^{t_2} Q\,dt}$ | Instantaneous power over instantaneous stroke volume (units: dP/dt) |
| Cardiac Efficiency | CE | $SW/M_yW$ | Efficiency of the heart in converting myocardial work into circulatory work |
| Cardiac Amplification | CA | d(SV)/d(LVEDV) | Marginal increase in stroke volume due to a marginal increase in LVEDV |
| Valvular Gradient | VG | ΔPmax | Maximum (during a cycle) pressure gradient across a valve |
| Valvular Gradient Reserve | VGR | d(VG)/d(LVEDP) | Increase in VG as a function of increase LVEDP. |

TABLE 1-continued

| Name | Variable | Equation | Description |
| --- | --- | --- | --- |
| Left Ventricle Pressure | LVP | Measured directly | Gauge pressure in Left |
| Valvular Area | VA | $0.11 * SV\sqrt{\Delta P}$ | Standard calculation of valvular area using mean ressure gradient and mean flow rate |
| Valvular Area Reserve | VAR | d(VA)/d(LVEDP) | Increase in valvular area as a function of increase in LVEDP |
| Valvular Regurgitation | VR | $\int Q_{REGURGITATION}$ | Cumulative regurgitant flow during a cycle |
| Valvular Regurgitatio Reserve | VRR | d(VR)/d(LVEDP) | Increase in regurgitant flow as a function of increase in LVEDP |

Some of the methods for measuring and calculating cardiac parameters according to principles of the present invention are described below. These methods are not an exhaustive list of the methods which may be employed according to the present invention as described in the appended claims.

Exemplary Methods for Determining Left Ventricular End-Diastolic Pressure (LVEDP), Left Ventricular End-Systolic Pressure (LVESP), and Aortic Pressure (AOP)

In one embodiment, catheter 102 may be used in a left heart catheterization procedure, and thus measure cardiac parameters relating to the left ventricle. Other embodiments, however, may be optimized for other chambers of the heart and, thus, may measure parameters in one or more of the other three chambers of the heart. Thus, LVEDP and EDP (End Diastolic Pressure) may be occasionally used interchangeably in this application, as LVEDP is merely one example of EDP.

In one embodiment, LVP (Left Ventricular Pressure) may be measured using a microfabricated pressure sensor attached to the catheter and introduced into the left ventricle. In alternate embodiments, an external pressure sensor is hydraulically linked by a lumen in the catheter to the body fluids of the left ventricle. Similarly, AOP is measured in some embodiments using a second microfabricated pressure sensor attached to the catheter. In alternate embodiments, AOP may be measured with the first microfabricated sensor or an external pressure sensor hydraulically linked to the aorta.

One method of determining LVEDP is to record left ventricular pressure (LVP) at point in time when left ventricular volume (LVV) is at a maximum, that is, just as the ventricle is about to contract. An alternate method comprises recording LVP at the "R" wave of the Q-R-S complex of an electrocardiogram (ECG). Another alternative comprises monitoring the left ventricular pressure continuously and using a pattern recognition algorithm to find the pressure when change in pressure divided by change in time equals zero (dP/dt=0) and $d^2P/dt^2$ is >0 just before dP/dt becomes maximum. Still another alternative method for determining LVEDP is to measure the pressure when the "first" heart sound "S1" stops, which occurs when the mitral valve is closed. To obtain the heart sounds, a pressure sensor may be used to sample the pressure signal at about 2000 times per second (or any other suitable frequency) and filter out the lower frequency components associated with increase in blood pressure. Alternatively, the catheter may employ a dedicated hydrophone for monitoring acoustic signals emanating from valves, intracardiac defects which produce shunts, regurgitant lesions or the like.

One method of determining LVESP is to record LVP when LVV is at a minimum, which is the point of minimum left ventricular volume. Another method of determining LVESP is to record LVP when the blood velocity in the aorta first becomes zero after reaching a maximum positive number, which is the point at which blood first stops flowing into the aorta. A significant difference between these two values might indicate and allow quantification of mitral regurgitant flow (or flow through shunts to the right side) after the aortic valve closes. An alternative method would be to record LVP when the "T" wave on the ECG has just ended. The pressures measured these three ways should give nearly identical results; therefore a comparison of any differences might help indicate a physiological abnormality. Another alternative method involves calculating a regurgitant fraction.

Method for Determining Left Ventricular End-Diastolic Volume

One currently used method for determining LVEDV employs one or more x-ray images of the heart and a manual drawing of the ventricular perimeter using an electronic cursor. These outlines are then used in conjunction with an empirical estimating formula to calculate an estimate of the heart's volume at end diastole. This technique is cumbersome and time consuming, making it impractical for estimating numerous end-diastolic volumes. In addition, since only one or two projections of the heart are used, a significant error is implied in the measurement. Furthermore, the formulae used in such techniques for calculating volume do not accurately reflect true volume.

Another currently available technique uses an external ultrasound transducer to image the whole heart and also measure volume. This is a fairly accurate technique, but since the ultrasound transducer is outside the body, it is incapable of simultaneously measuring pressure or changing end diastolic pressure. In addition, not all patients have anatomy which is amenable to an ultrasonic imaging system transthoracically. Nevertheless, this approach could be used in conjunction (simultaneously) with a catheter that doesn't feature the volume-measuring capability.

Figure 10:
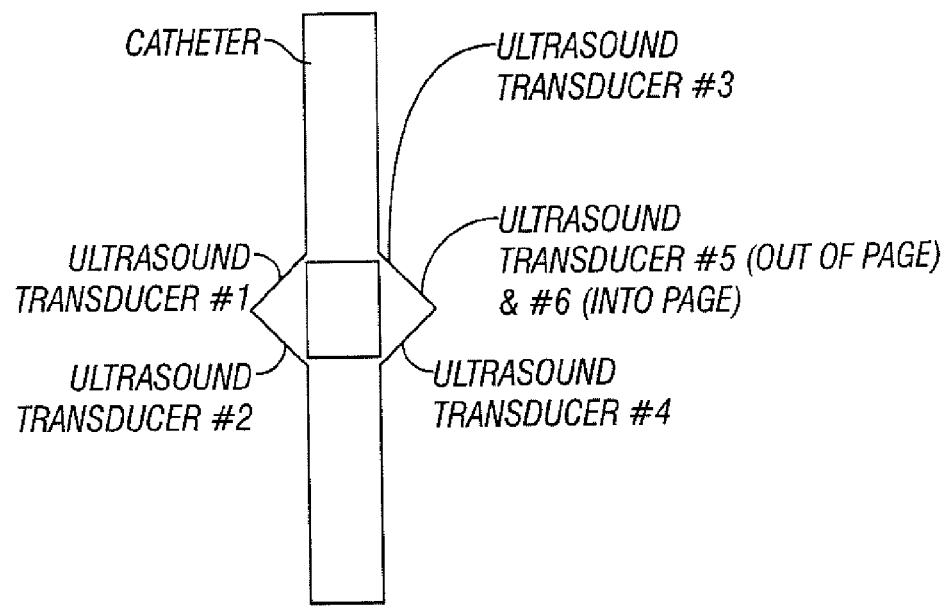
FIG. 10 illustrates a sensor having multiple ultrasound transducers, as may be used in an embodiment of the present invention.

In one embodiment of the present invention, a method of measuring volumes in body cavities such as a heart chamber, involves using six ultrasound transducers mounted orthogonally to each other, as shown in FIG. 10. Two of the transducers are mounted parallel to the catheter and thus measure a distance perpendicular to the axis of the catheter. The other four transducers are mounted in pairs on surfaces that are axially 90 degrees rotated from the first pair of sensors but also tilted 45 degrees up or down. Thus, the latter four transducers measure the distance between them and the wall of a heart chamber in four directions which are all orthogonal to each other. Another way of describing the arrangement is that of six transducers each mounted on a face of a cube. The cube is then rotated 45 degrees about one of the faces and mounted over a catheter body. To facilitate manufacturing of the catheter while keeping a slim profile, the cube may be "disassembled," i.e., the transducer pairs are not necessarily contiguous. The transducer assembly might also be part of an inflatable or expandable assembly to project into the ventricle somewhat during measurement.

An alternative method for measuring ventricular volumes is to use a phased array ultrasonic imaging system with circular electrodes, i.e. rings about the catheter. These rings may be excited slightly out of phase with each other to send the wave up or down relative to the perpendicular of the catheter. The signals returning to the rings would be distributed over time, depending upon the distance from the catheter to the ventricular wall in the various segments of the ring. Thus, the amplitude over time of the reflected signal would correspond to the various radial distances between the catheter and the wall of the heart chamber. Making numerous measurements at various angles from normal in a very short period, the system makes multiple cross-sectional area measurements of the ventricle that are then added using Taylor's method for estimating volumes (similar to what is done using external ultrasonic arrays). Yet a third method of measuring ventricular volumes would be to use two pairs of planar phased array sensors, each parallel pair perpendicular to the other, so that four sides of a catheter are mounted with a phased array transducer. Each of the sensors may, as above, measure a distance to the wall in order to measure, at any given angle from the transducers, four radii to the ventricular wall. Taylor's method is then used as before to estimate true ventricular volume.

One method of estimating LVEDV is to record LVV, measured using one of the above methods, at the point of time when it is at a maximum. In an alternative method, an array of electrical conductance sensors on the catheter is used to determine the average conductance of the ventricular blood. A volume of liquid with a known and different electrical conductivity is dispersed into the left ventricle during diastole. At end diastole and during systole, the conductivity in the ventricle is monitored. These measurements produce an estimate of the diluted electrical conductance of the ventricular blood. Then, knowing the volume of injected blood ($V_I$), the electrical conductance of the injected blood ($k_I$), the conductance of the undiluted blood ($k_B$), and the conductance of the diluted blood ($k_D$), one may compute the end diastolic volume using the following equation:

$$V_D = V_I \frac{k_I - k_B}{k_D - k_B}$$

Another method of estimating end diastolic volume uses an array of temperature sensors on the catheter to determine the temperature of the blood. A quantity of blood at a lower temperature is injected into the ventricle during diastole. The temperature of the diluent may be measured just before it leaves the catheter, to improve accuracy. Then, knowing the volume of injected blood ($V_I$), the specific heat of the blood ($C_B$), the specific heat of the diluent ($C_I$), the undiluted temperature of blood ($T_B$), the temperature of the diluent ($T_I$), and the average temperature of the diluted blood at end diastole ($T_D$), the end diastolic volume ($V_D$) is given by the following equation:

$$V_D = V_I\left(1 + \frac{C_I(T_D - T_I)}{C_B(T_B - T_D)}\right)$$

In another embodiment, a method of estimating end diastolic volume uses an array of light sources and optical sensors, perhaps incorporating optical fibers. A volume of a solution containing a dye of a known concentration is injected and dispersed into the ventricle during diastole. The concentration of dye in the blood may be measured using either absorption or fluorescent techniques. A dye may be any marker, such as a liquid, gas, other fluid or the like. A fluorescent technique, for example, would entail shining light of one wavelength into the blood and detecting the intensity of light at a different (fluorescent) wavelength. The concentration of dye in the blood would be a linear function of the ratio of the intensity of the fluorescent light over the intensity of the exciting light. Then, knowing the volume of injected blood ($V_I$), the concentration of dye in the undiluted blood ($D_B$), the concentration of dye in the diluent ($D_I$), and the average concentration of dye in the diluted blood at end diastole ($D_D$), the end diastolic volume ($V_D$) is given by the following equation:

$$V_D = V_I \frac{D_B - D_I}{D_B - D_D}$$

In other embodiments, it may be useful to determine an end-diastolic volume without introducing fluid to the ventricle. In some embodiments, it may even be useful to reduce the end-diastolic volume or end-diastolic pressure from the resting value. To accomplish this, a catheter may include a balloon that can hold at least as much volume as the diluent (either thermal, conductive, or dye diluent or none if ultrasound is used to measure volume, as in the preferred method). The balloon is first inflated in the ventricle during the systolic phase of the previous cycle, helping to eject a corresponding amount of blood from the ventricle. To determine the end-diastolic volume without influencing it, the balloon is simultaneously and completely deflated during diastole by a volume equal to the volume of diluent injected into the ventricle at the same time. Thus, as the balloon shrinks, the diluent is added to the ventricle without increasing or decreasing the pressure in the ventricle. It may be useful to decrease the end-diastolic volume and/or end-diastolic pressure from an at-rest state while determining the end-diastolic volume. This may be accomplished by first inflating the balloon during the systolic phase or, in the case of repeated cycles, just after the aortic valve has closed. Then, during diastolic filling of the ventricle, an amount of diluent is dispersed into the ventricle. The balloon is simultaneously and completely deflated by a volume greater than the volume of diluent added, reducing the end diastolic pressure and volume. The end-diastolic volume is determined using one of the dilution methods described above. In one embodiment, one or more ultrasound transducers are used to measure the ventricular volume continuously while the balloon is inflated during systole and deflated in diastole to reduce the end-diastolic pressures and/or volumes.

Methods for Determining End-Systolic Volume

One method for measuring LVESV is to record LVV when it is at a minimum, using one of the continuous volume measuring systems. An alternative method for measuring for LVESV is that LVV when aortic flow rate is first zero following its maximum. The difference in volumes of these two recordings is equal to the combination of mitral regurgitant flow and left-to-right shunt flow after the aortic valve is closed.

Methods for Determining Ejection Fraction

Ejection Fraction is typically defined as the ratio of the difference between end-diastolic volume and end-systolic volume over end-diastolic volume. This calculation may be made, using any of the above-described methods of measuring EDV and ESV.

Methods for Determining Cardiac Output, Cardiac Index, Stroke Volume, and Stroke Volume Index on a Per-Stroke Basis In one embodiment, a blood velocity or flow rate sensor is coupled with the catheter and inserted into the aorta. This sensor samples the velocity of blood at regular intervals, such as approximately once every millisecond, and transmits that information to a controller or other processor. The controller then determines the average blood velocity by averaging the readings taken over a second (or some other similar period of time that is representative of the next step). During that sampling time, the cardiac output is independently measured using one of the accepted methods, such as Fick's Law using oxygen consumption or a dilution method (thermal dilution, conductance dilution or dilution with a marker, such as a gas, other fluid, liquid, dye or the like). (Grossman's *Cardiac Catheterization and Angiography*, pp. 101–117 describes these methods in detail). The cardiac output thus measured is divided by the average velocity or flow rate to determine a scaling coefficient. This coefficient assumes that the aortic cross section near the velocity or flow rate sensor is reasonably constant during the sampled cycle and successive cycles. A number of different methods of measuring blood velocity or flow rate are possible, including thermal dilution, shear force measurement, a pitot-tube method (stagnant versus dynamic flow), Ultrasound Doppler, and/or any other suitable method. Once the scaling factor has been determined, the stroke volume may be determined for any given cycle and is equal to the product of the scaling factor and the integral of velocity through that cycle. The stroke time is also calculated as that period between successive end-diastolic events. Cardiac output is then calculated as the ratio between stroke volume over stroke time, adjusted to correct units. Cardiac index is cardiac output divided by body surface area (BSA), which is a known value based on a patient's height and weight. Stroke volume index is stroke volume divided by BSA.

Methods for Determining Cardiac Reserve and Cardiac Reserve Index

In one embodiment, a method for measuring cardiac reserve involves first measuring LVEDP and/or LVEDV at the beginning of one cardiac cycle and then measuring the cardiac output during that cycle using the methods described above. This measurement may be repeated any number of times and multiple data pairs (LVEDP, CO) may be taken. Then, an amount of fluid is injected into the left ventricle during a diastole period and the resulting end-diastolic pressure recorded. The cardiac output for that cycle is recorded using the methods described above and a new data point (LVEDP, CO) is recorded. This process is repeated as desired to create a set (n>=2) of data pairs. A line of regression is then fit through the data points using a least-squares technique. The slope of that line is equal to cardiac reserve. Cardiac reserve index is equal to cardiac reserve divided by BSA.

Methods for Determining Stroke Reserve and Stroke Reserve Index

One method of measuring cardiac reserve is to first measure the LVEDP and the beginning of one cardiac cycle and then measuring stroke volume during that cycle using the methods described above. This measurement may be repeated any number of times and multiple data pairs (LVEDP, SV) taken. Then, an amount of fluid is injected into the left ventricle during a diastole period and the resulting end-diastolic pressure recorded. The stroke volume for that cycle is recorded using the methods described above and a new data point (LVEDP, SV) is recorded. This process is repeated as desired to create a set (n>=2) of data pairs. A line of regression is then fit through the data points using a least-squares technique. The slope of that line is equal to stroke reserve (SR). Stroke reserve index (SRI) is equal to SR divided by BSA.

Methods for Determining Myocardial Work, Myocardial Work Index, Myocardial Work Reserve, and Myocardial Work Reserve Index Myocardial work ($M_YW$) comprises the work performed by the myocardium against the blood in the heart during a single heart cycle. It is mathematically defined as the integral of Pressure and dV as V varies from V(max) to V(min) minus the integral of Pressure and dV as V varies from V(min) to V(max). Thus it is the work performed by the heart tissue during systole minus the work performed on the heart tissue by the body during diastole. Myocardial work may thus be expressed as the difference between the integral of the pressure and volume while the volume is decreasing from the integral of the pressure and volume while the volume is increasing:

$$SW = \int_{dV/dt<0} Pdv - \int_{dV/dt>0} PVdv$$

Myocardial work index (MWI) is equal to the myocardial work divided by BSA.

In some embodiments, it may also be advantageous to calculate the first moment of work, which could also be useful for optimization. The first moment of work is calculated as:

$$SW = \int_{dV/dt<0} PVdv - \int_{dV/dt>0} PVdv$$

Myocardial work index (MWI) is equal to the myocardial work divided by BSA.

In one embodiment, myocardial work reserve is calculated by first recording the LVEDP of a given heart cycle and then calculating the myocardial work during that cycle. This measurement may be repeated any number of times and multiple data pairs (LVEDP, $M_YW$) taken. Then, an amount of fluid is injected into the left ventricle during a diastole period and the resulting end-diastolic pressure recorded. The myocardial work for that cycle is recorded using the methods described above and a new data point (LVEDP, $M_YW$) is recorded. This process is repeated as desired to create a set (n>=2) of data pairs. A line of regression is then fit through the data points using a least-squares technique. The slope of that line is equal to Myocardial reserve ($M_rR$). Myocardial reserve index (MRI) is equal to myocardial reserve divided by BSA.

Figure 4A:
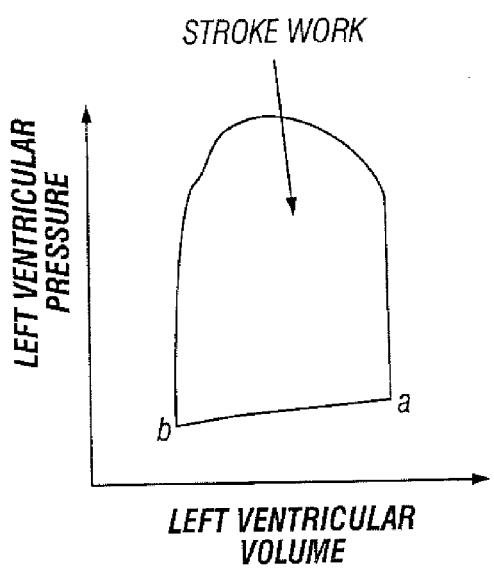
FIG. 4A illustrates a pressure/volume curve which may be derived according to principles of the present invention in some embodiments.
Figure 4B:
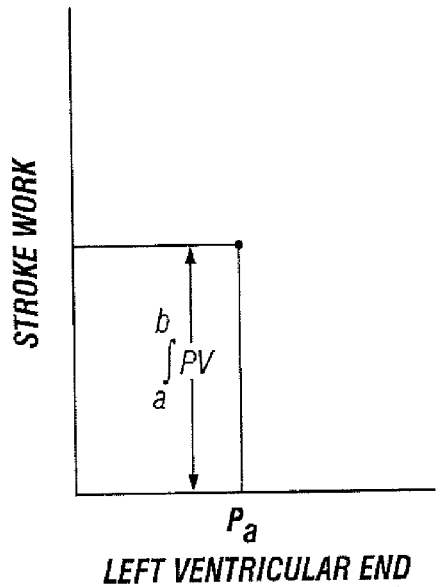
FIG. 4B illustrates a stroke work/pressure curve which may be derived according to principles of the present invention in some embodiments.

Methods for Determining Stroke Work, Stroke Work Index, Stroke Work Reserve, Stroke Work Reserve Index, and Cardiac Efficiency Stroke work (SW) is typically defined the work performed by the left ventricle on the circulatory system. This relationship is displayed in graphic form in FIGS. 4A and 4B. In one embodiment of the present invention, stroke work is determined by calculating the integral of the product of volume ejected into the aorta and pressure increased by the ventricle. In some embodiments, the average filling pressure is determined and subtracted from the ventricular pressure during systole. This difference is then multiplied by the quantity of blood flowing into the aorta. This product is then integrated over a single stroke to calculate stroke work.

$$SW = \int_{cycle} V_{Aorta}(P_{systole} - \overline{P_{diastole}})$$

Thus, SW is distinguishable from myocardial work. The difference between these two parameters involves a difference in how regurgitant flow plays into the measurements. Myocardial work measures the work that the heart muscle performs, while SW measures the work the heart performs against the circulatory system. Cardiac efficiency (CE), yet another parameter which may be measured according to the present invention, is defined as the ratio of SW over myocardial work and is a measure of the efficiency with which the heart converts myocardial work into stroke work. This parameter may be used, for example, by biventricular pacing devices, pharmaceutical intervention, and other interventions to optimize their performance.

In an alternative embodiment, stroke work may be calculated by taking the integral of the product of aortic pressure and aortic flow rate minus the integral of the product of left atrial pressure and flow through the mitral valve. With either of the two methods described above, the stroke work index is equal to stroke work divided by BSA. A similar set of calculations is possible for the right ventricle, where stroke work would be the integral of the product of the pressure in the Pulmonary Artery times the systolic volume flowing into the Pulmonary Artery minus the integral of the right atrial pressure times the diastolic volume flowing into the right ventricle.

In some embodiments, stroke work reserve is calculated by first recording the LVEDP of a given heart cycle and then calculating the stroke work during that cycle. This measurement may be repeated any number of times and multiple data pairs (LVEDP, SW) taken. Then, a predetermined amount of fluid is injected into the left ventricle during a diastole period and the resulting end-diastolic pressure recorded. The stroke work for that cycle is recorded using the methods described above and a new data point (LVEDP, SW) is recorded. This process is repeated as desired to create a set (n>=2) of data pairs. A line of regression is then fit through the data points using a least-squares technique. The slope of that line is equal to stroke work reserve (SWR). Stroke work reserve index (SWRI) is equal to SWR divided by BSA.

Methods for Determining Cardiac Amplification

Cardiac amplification (CA) may be defined as the marginal increase in stroke volume due to a marginal increase in end-diastolic volume. In one embodiment, cardiac amplification is calculated by first recording the LVEDV of a given heart cycle and then calculating the stroke volume during that cycle. This measurement may be repeated any number of times and multiple data pairs (LVEDV, SV) taken. Then, an amount of fluid is injected into the left ventricle during diastole and the resulting end-diastolic volume is measured. The stroke volume for that cycle is measured using the methods described above and a new data point (LVEDV, SV) is recorded. This process is repeated as desired to create a set (n>=2) of data pairs. A line of regression is then fit through the data points using a least-squares technique. The slope of that line is equal to cardiac amplification.

Methods for Determining Valvular Gradient, Valvular Gradient Reserve, Valvular Area, Valvular Area Reserve, Valvular Regurgitation, Valvular Regurgitation Reserve, and Valvular Resistance In one embodiment, valvular pressure gradient (VG) may be measured directly using two pressure sensors one upstream and the other downstream of a heart valve, as in the aortic valvular pressure gradient. In another embodiment, VG may be measured somewhat indirectly, as in the case of the mitral valve, where upstream pressure may be measured using a known pulmonary capillary wedge pressure measurement technique and downstream pressure is measured in the left ventricle. In either case, a pressure gradient across a valve may be measured throughout the appropriate filling period while the flow through the valve is simultaneously determined. In the case of an aortic valve, the flow through the valve is measured using the aforementioned scaled velocity sensor in the aorta; in the case of the mitral valve, the flow is measured as the diastolic change in ventricular volume minus any regurgitant aortic flow measured by the scaled velocity sensor in the aorta. Throughout the filling period, multiple data pairs are recorded in the form of ($\Delta P$, Q), where $\Delta P$ is the pressure gradient and Q is the instantaneous volumetric flow rate through the valve. The maximum pressure gradient ($\Delta P$) and mean pressure gradient during any cycle may then be recorded as the VG for that cycle.

The total regurgitant flow through the valve in a cycle—valvular regurgitation (VR) may be calculated as the integral of the reverse volumetric flow rate during a cycle. In the case of aortic, pulmonic or tricuspid regurgitation, this flow may be directly determined using the output of the scaled velocity sensor, and is the scaled integral of all negative volumetric flow rates during a cycle. In the case of the mitral valve, regurgitant flow may be determined by subtracting the stroke volume (measured in the aorta using the scaled velocity sensor) from the difference between the maximum and minimum left ventricular volumes (LVEDV–LVESV). Thus mitral regurgitant flow, in the absence of shunts, is equal to LVEDV–LVESV–SV. In some embodiments, measurement of mitral regurgitation may include factoring in any aortic regurgitation that is present. Since calculating stroke volume includes subtracting regurgitant (diastolic) aortic flow from the total amount of blood ejected into the aorta during a given cycle, in some embodiments the amount of aortic regurgitation is added back in to give a more accurate measurement of mitral regurgitation. Therefore, MR=LVEDV–LVESV–SV+AR, where MR is the net systolic mitral regurgitant flow, and AR is the net (diastolic) aortic regurgitant flow.

To calculate the effective area of a valve, one embodiment uses a known formula (the Gorlin Formula—see Grossman's *Cardiac Catheterization and Angiography*, p143). Using the known formula, average flow rates such as cardiac output and mean pressure gradients are used to calculate a mean orifice area. So, this embodiment uses these mean values to calculate the effective valvular area. The equation for mean mitral valve area (MMVA) is $$\frac{CO/(HR*DFP)}{(44.3*0.85)\sqrt{\Delta P}},$$

where CO is Cardiac Output in cc/min, HR is beats/min, DFP is filling period in seconds/beat, and $\Delta P$ is the mean pressure gradient across the mitral valve in mm Hg. This technology enables the real time estimate of valvular area by using instantaneous measures of flow rate and pressure gradient. Thus mitral valve area (MVA) is $$\frac{Q}{(44.3*0.85)\sqrt{\Delta P}},$$

where Q is the volumetric flow rate through the valve at any point in time and $\Delta P$ is the pressure gradient at approximately the same point in time. (This pressure gradient is typically measured with the assistance of a right heart catheter and is the difference between the pulmonary capillary wedge pressure from the left ventricular pressure). With this equation—modified from Gorlin and Gorlin's original—it is possible to measure orifice diameter as a function of time.

A similar equation is found for the aortic valve: mean aortic valve area (MAVA) is $$\frac{CO/(HR*SEP)}{(44.3)\sqrt{\Delta P}},$$

where SEP is the Systolic Ejection Period and $\Delta P$ is this time the pressure gradient across the aortic valve. Similarly, a real time measurement of aortic valve area (AVA) is $$\frac{Q}{(44.3)\sqrt{\Delta P}},$$

where Q is the instantaneous volumetric flow rate through the aortic valve, as measured using the scaled velocity sensor in the aorta and $\Delta P$ is the pressure gradient across the aortic valve.

In one embodiment, variations in the above-described parameters (regurgitant flow, valvular area, and pressure gradient) with increasing cardiac output, are measured. One method for measuring such variations comprises first measuring LVEDP for a given heart cycle. At the completion of that cycle, additional parameters related to a valve are measured—for example, valvular regurgitation(VR), valvular area (VA), and valvular pressure gradient (VG). Any number of these cycles may be recorded, so that multiple measurements may be averaged together. On a successive cardiac cycle, an amount of fluid is introduced into the left ventricle during diastole to increase end-diastolic pressure and the resultant values are again measured, typically (but not always) with a higher cardiac output (resulting from the higher LVEDP). Multiple data sets are thus generated. To obtain the valvular gradient reserve (VGR), a least squares method is used to fit a line is fit between the multiple data pairs (LVEDP, VG). The slope of that curve is VGR. As cardiac output doubles, the pressure gradient should quadruple, so VGR would be expected to increase with increasing cardiac output. It nevertheless represents the marginal increase in gradient with increasing LVEDP within the corresponding range of LVEDP.

In various embodiments, valvular area reserve (VAR) may be obtained by using a least squares method to fit a line between the various data pairs (LVEDP, VA). The slope of that fit line is VAR, which represents the marginal increase in valvular area due to a marginal increase in LVEDP. There are some patient populations (some disease states) where the effective area decreases with increasing cardiac output, and this value would be negative for that class of patient.

Similarly, valvular regurgitation reserve (VRR) may be obtained by using a least squares method to fit a line between the various data pairs (LVEDP, VR). The slope of this line is VRR, which represents the marginal increase in valvular regurgitation due to a marginal increase in LVEDP. Any of these "reserve" measurements could be made relative to cardiac output (or LVEDV, or any other variable), instead of LVEDP.

Methods for Generating Frank-Starling Curves

A Frank-Starling (F-S) curve has many definitions in the literature. They all generally relate to the change in hemodynamic output of the left ventricle due to changes in the left ventricular end-diastolic volume (LVEDV) or left ventricular end-diastolic pressure (LVEDP). The most common types of F-S curves are: Cardiac Output v. LVEDP, Cardiac Output v. LVEDV, Stroke Work v. LVEDP, Stroke Work v. LVEDV, and LVESP/LVEDP v. LVEDV.

In some embodiments, an F-S curve places Cardiac Output (CO) on a vertical axis and LVEDP on a horizontal axis. The catheter system records the LVEDP at the beginning of one or more heart cycles and then calculates the CO at the end of each corresponding cycle. By introducing and/or removing fluid (or increasing or reducing the volume of an inflatable balloon), the system adjusts the end-diastolic pressure to a new value and measures that value. It then calculates the resulting cardiac output for that cycle. By repeating this process over several cardiac cycles, each using a different LVEDP as it's starting point, a graph of CO v. LVEDP is generated, recorded, and displayed to be seen by the physician.

In other embodiments, an F-S curve that represents Cardiac Output v. LVEDV may be generated. Any of the above-described methods may be used for measuring CO on a per stroke basis and LVEDV on a per stroke basis. Then, by introducing and/or withdrawing amounts of fluid from the ventricle during diastole, one may vary the LVEDV for one or more cycles of the heart. If a reduced starting volume of the heart is desired, for example to simulate a reduction in preload, a balloon may be attached to the catheter and inflated during the systolic phase of the previous heart cycle. The balloon is then deflated during diastole to simulate a reduction in preload.

Another variation of an F-S curve is to have either myocardial work (MyW) or stroke work (SW), both defined above, on the vertical axis and LVEDP on the horizontal axis. The difference between the two measures is an important indicator of valvular disease related to the left ventricle. In a manner similar to that described above for CO v. LVEDP, the system may be used simultaneously calculate MyW and SW for each LVEDP. Cardiac efficiency (CE), the ratio of SW over MyW, may also be calculated and displayed, showing how the efficiency of the heart changes at increasing levels of LVEDP and perhaps correspondingly increasing levels of cardiac output. Any of the above-described parameters may be plotted against any other suitable parameter or parameters, as desired.

In one embodiment, to generate a CO v LVEDP curve, a real-time cardiac output sensor is coupled with the catheter so that it resides in the aorta. This real time sensor may be calibrated using one or more of several accepted methods of measuring cardiac output, such as Fick's method based on oxygen consumption or the dilution method. The CO sensor may be used to measure the volume of blood ejected from the left ventricle during each cycle. At the same time, another sensor on the catheter measures pressure inside the left ventricle. During diastole, the catheter system introduces saline or other fluid into the left ventricle and measures the resulting LVEDP. Then, as the heart completes its cycle, the CO sensor measures the output of the heart during that cycle. The result represents a single point on the CO v LVEDP curve. After some period of time, a second point is plotted on the curve by injecting a second bolus of saline or other liquid into the left ventricle during diastole. The cardiac output and LVEDP are then measured for that cycle and the second point is plotted. Additional points are generated during successive cycles and as various LVEDP conditions are created, as desired.

In another embodiment, an F-S curve based on a different definition of stroke work is generated using a method similar to the one just described. Stroke work is calculated simultaneously (or nearly simultaneously) with cardiac output (i.e. during the same cycle). One definition of stroke work which may be used is the integral of the product of pressure and stroke volume during a single cycle. Another definition uses the change in volume of the ventricle to determine the work performed by the heart. This latter measurement, however, includes work required to pump regurgitant flow retrograde against the mitral valve as well as work lost to regurgitant aortic flow. In an additional embodiment, the stroke work is the product of the volume of blood ejected into the aorta multiplied by the pressure gradient between the ventricle and the aorta. The volume of blood ejected into the aorta is measured by the blood velocity sensor and the pressure gradient is measured using the difference between two pressure sensor, one in the ventricle and the other in the aorta near the velocity sensor.

As previously discussed, catheters in many embodiments of the present invention include means for effecting end-diastolic pressure and/or volume by introducing and/or withdrawing an amount of fluid (such as saline, glucose, or any other suitable fluid) into or from the ventricle at a desired time during a heart cycle, such as during diastole. In one embodiment, fluid introduction is achieved by driving an external actuator, such as a pump, coupled with the catheter using control signals from the controller, such as a computer or other data processor. The timing of fluid introduction and/or withdrawal may be based upon measurements taken via a pressure sensor in the heart chamber. Such measurements may be taken at any suitable interval, but in some embodiments they are taken at a rate of about 1000 Hz.

Methods for Generating Pressure/Volume Loops

Figure 11:
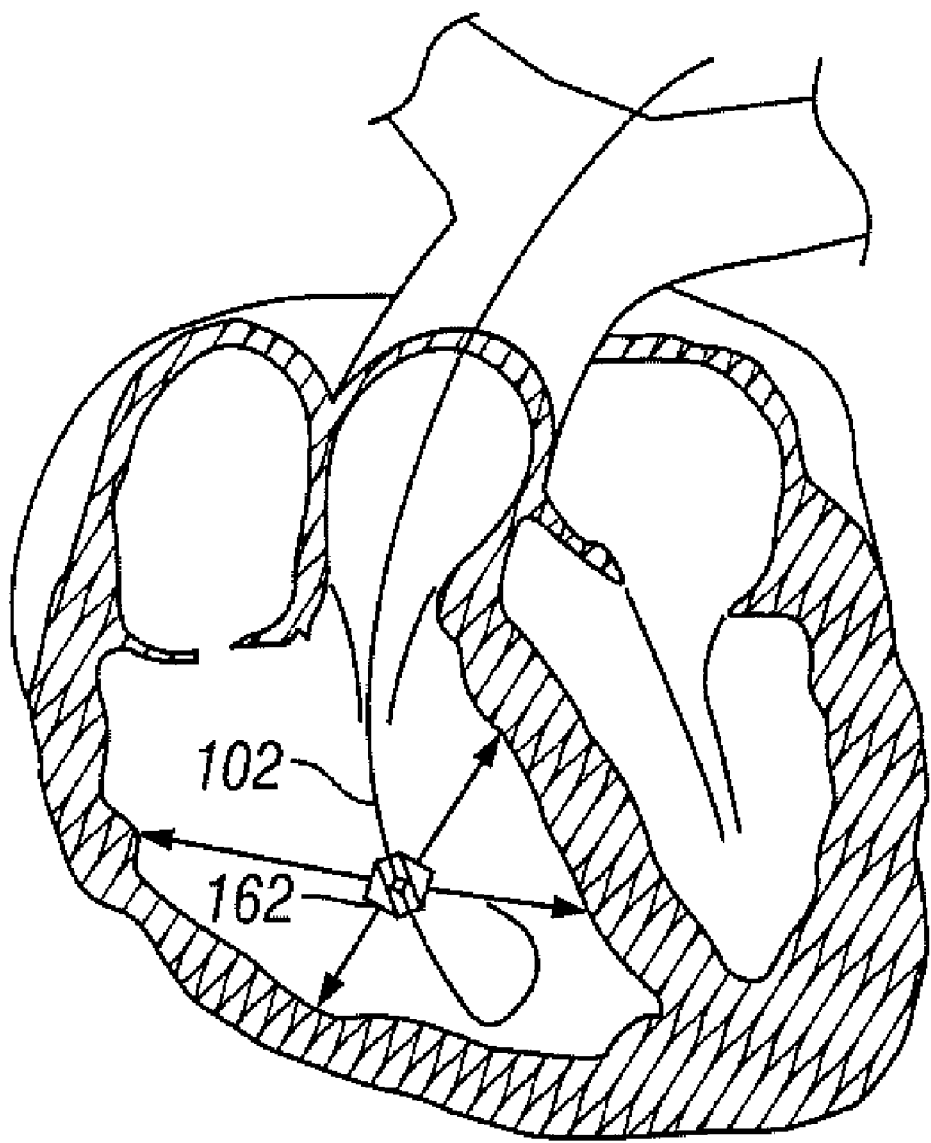
FIG. 11 illustrates a catheter in place in a patient's heart, having an ultrasound sensor such as the one illustrated in FIG. 10.

With reference now to FIGS. 4–9, information which may be generated and optionally displayed according to one embodiment of the invention is shown. This information is generally referred to as "pressure-volume loops," and such information may be displayed in various forms. In one embodiment, a catheter is used to generate pressure-volume loops by measuring on a simultaneous or near-simultaneous basis intracavitary pressure and volume. The volume may be measured, for example, using six orthogonally oriented ultrasound transducers, as described in detail above. Referring to FIGS. 10 and 11, one embodiment of such a six-transducer device 162 on a catheter 102 is shown. As designated by the arrows in FIG. 11, the six transducers may be used to measure six distances from the transducer device 162 to various locations on the inner wall of the heart chamber. These six distances represent radii of curvature to an inscribed ovoid. One or more phased array transducers may alternatively be used to measure volume. In one embodiment, multiple phased array transducers have at least two arranged axially about the axis of the catheter. In another embodiment, four phased array sensors are arranged axially around the catheter.

Pressure may be measured using readings from one or more pressure sensors located inside the cavity (i.e., the left ventricle in FIG. 11, but any other suitable heart chamber or other cavity is contemplated). In some embodiments, the pressure sensor used in the heart chamber comprises an absolute pressure sensor, so that a pressure sensor sampling the ambient pressure is often used as well, to enable the calculation of a gauge pressure with which most physicians are familiar. This gauge intracavitary pressure comprises the absolute intracavitary pressure minus the absolute ambient pressure. In various embodiments, an ambient absolute pressure sensor may be coupled with the catheter outside of the body or, alternatively or additionally, may be coupled with a controller, a console, and/or the like.

Figure 5A:
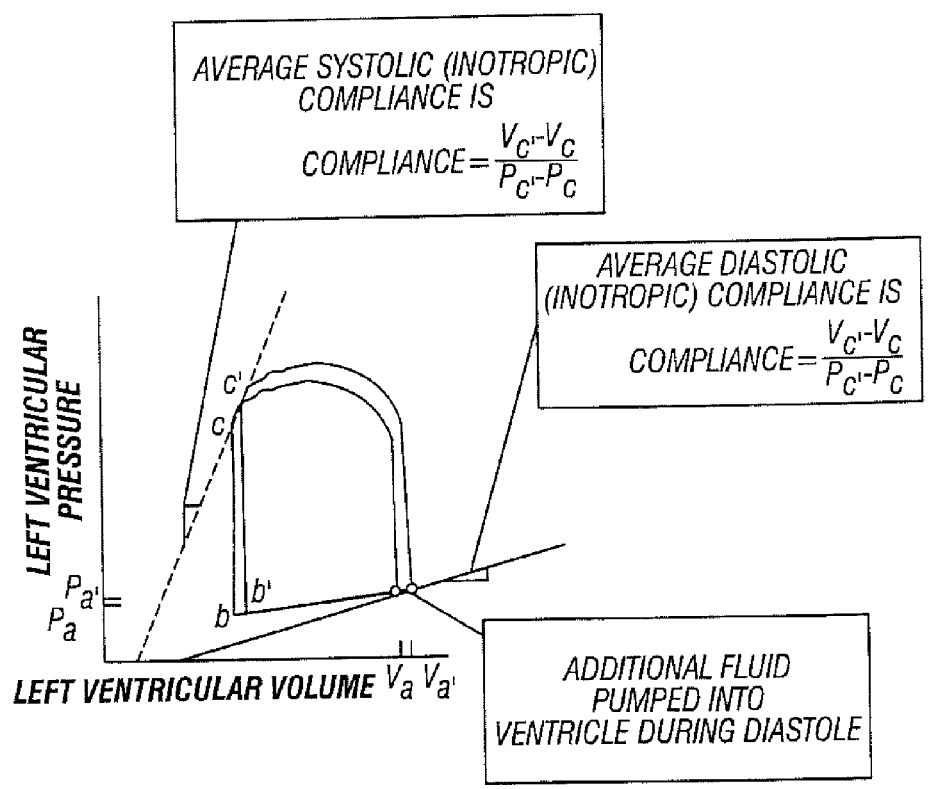
FIG. 5A illustrates an induced change in pressure/volume curves which may be derived in some embodiments, according to principles of the present invention.
Figure 5B:
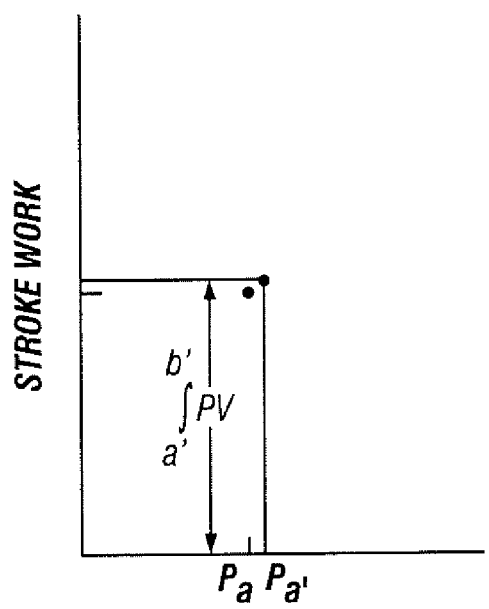
FIG. 5B illustrates the induced change according to FIG. 5A in a stroke work/pressure curve.

Referring now to FIGS. 5A and 5B, one method of the present invention involves introducing fluid (or inflating an expandable balloon) inside a heart chamber such as the left ventricle during diastole to cause a shift in a pressure/volume loop. The original loop is shown as the points a, b, and c, while the shifted loop (up and to the right) is shown as points a', b', and c'. Generally, introducing a fluid into the left ventricle during diastole may result in a different end-diastolic pressure and/or volume, which may be measured and shown graphically as a shifted pressure/volume curve.

By introducing and/or withdrawing fluid into/from the ventricle during diastole, various end-diastolic pressure and volume conditions for the ventricle are created. The resulting pressure and volume of the ventricle may then be measured continuously as the heart completes its cycle. The integral of pressure multiplied by volume (as measured during one heart cycle) is equal to the stroke work, as shown by the area inside the curve in FIG. 5A and on the vertical axis in FIG. 5B. Stroke work as a function of end diastolic pressure is one measure of ventricular performance. Pressure/volume loops, as in FIGS. 4A and 5A, may be used to generate Frank-Starling curves, which may include any of a number of various parameters, as described in detail above. This is a vast improvement over conventional methods for generating Frank-Starling curves, which involve measurements taken over a period of days using a Swan-Ganz catheter to measure cardiac output, as well as administration of one or more medications to vary the LVEDP.

Referring again to FIGS. 5A and 5B, in some embodiments of the invention, methods may be used to calculate myocardial stiffness and/or compliance of the heart chamber in which a catheter is positioned. In one embodiment, a method of calculating myocardial stiffness involves first measuring pressure and volume when volume is at a maximum (i.e., at end of diastole) and then again when volume is at a minimum (i.e., end of systole). During a subsequent heart cycle, end-diastolic pressure and volume are increased (or decreased) using one or more actuator on the catheter, and the two sets of data points are recorded again. Any suitable number of such pairs of data points may be measured, and they may then be used to generate a pressure/volume curve. A least squares routine may then be used for each set of data pairs (i.e., the end-diastolic set and the end-systolic set) to fit a straight line between each set of points. The slope of the line through the end-diastolic points is the lusitropic stiffness of the heart, and the inverse of that slope is the lusitropic compliance. The slope of the line through the end systolic points is the inotropic stiffness and the inverse of that slope is the inotropic compliance. These measurements and equations used for calculations are shown as labels on FIG. 5A.

In another embodiment, a method of measuring the compliance of a heart chamber involves continuously varying the volume in the chamber and simultaneously measuring pressure in the chamber to give a continuous measure of chamber wall stiffness. In this method, a hydrophone may be used to vary the volume inside the ventricle at any suitable frequency, such as approximately 200 times per second. A pressure sensor is used to measure pressure change at approximately the same frequency at which it is being effected by the hydrophone. By filtering the pressure signal at 200 Hz, one obtains a signal whose amplitude is proportional to the stiffness of the heart throughout the cycle. The inverse of this number is the compliance of the heart throughout the cycle. When either valve to the ventricle is open, the method measures the effective stiffness and compliance of the hydraulically linked chamber. Thus, when the mitral valve is open, the stiffness and compliance of both the left atria and the left ventricle, as well as some of the pulmonary vein, may be measured. When the mitral valve is closed and the aortic valve is open, the combined stiffness of the left ventricle and the aorta may be measured. When both valves are closed, as in isovolumic contraction or isovolumic relaxation, then the stiffness of the left ventricle alone may be measured. Since the pressure/volume slope is rather steep during either isovolumic phase, it may be desired to use a higher frequency such as 1000 Hz or even 5000 Hz to measure stiffness and compliance and how those values change during contraction or relaxation.

Figure 6:
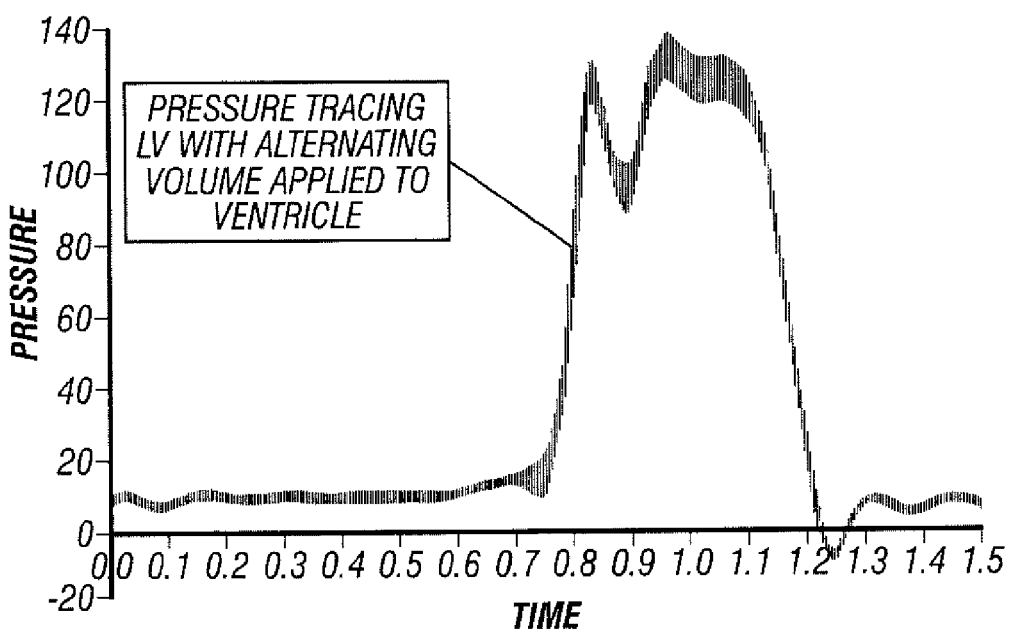
FIG. 6 illustrates a change in pressure in a heart chamber over time, the change induced by an actuator according to principles of the present invention.
Figure 7:
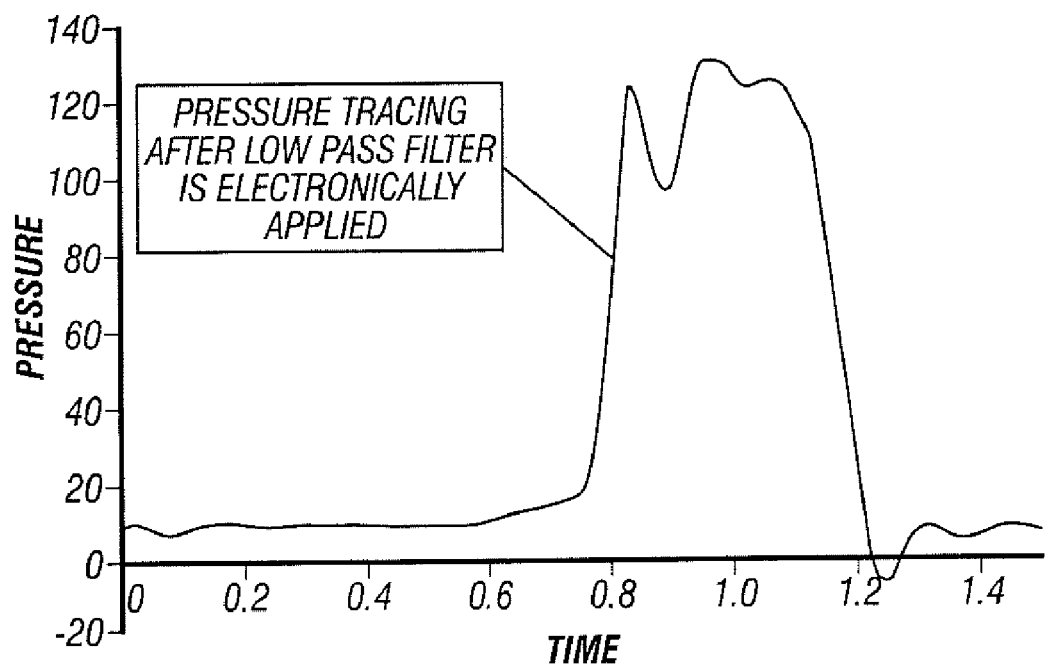
FIG. 7 illustrates data such as shown in FIG. 7 after passing through a low-pass filter according to principles of the present invention.
Figure 8:
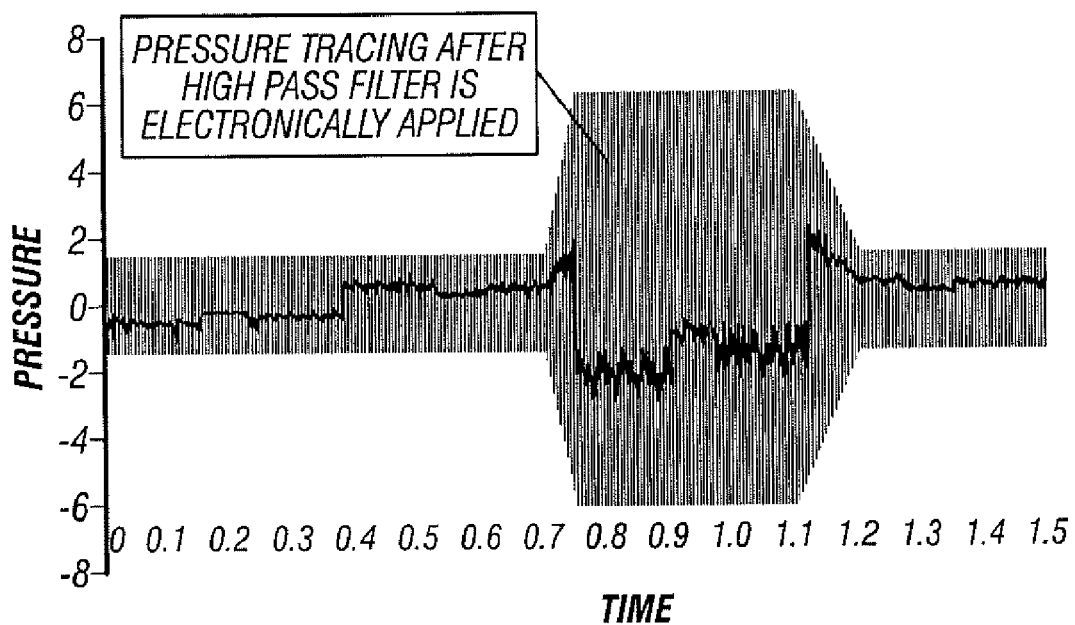
FIG. 8 illustrates data such as shown in FIGS. 6 and 7 after passing through a high-pass filter according to principles of the present invention.
Figure 9:
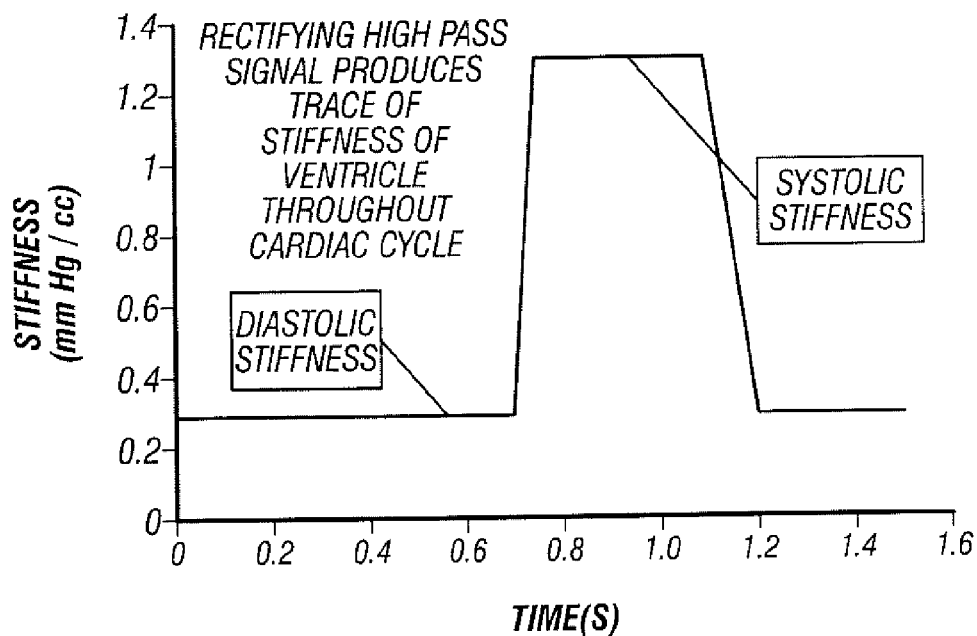
FIG. 9 illustrates stiffness of a heart chamber over time, as derived from data such as that illustrated in FIGS. 6–8 according to principles of the present invention.

FIGS. 6–9 show various ways in which changes in pressure, and thus stiffness, may be displayed over a period of time. FIG. 6 shows a change in pressure when an actuator is used to effect an oscillating volume change. FIG. 7 shows the same change, after being processed through a low-pass filter. FIG. 8 shows the same change, after being processed through a high-pass filter. Finally, FIG. 9 shows the same data as it relates to systolic and diastolic stiffness of the heart chamber.

Methods for Determining Dose/Response Characteristics of Medications

In yet another embodiment, a method of the present invention may be used to measure one or more dose/response characteristics of a medication on various cardiac and/or circulatory functions. Because most patients have somewhat unique responses to a given medication, knowing the dose/response curve of any medication allows for a quantitatively based selection among similar medications, quantitative prediction of optimal dosing levels of the chosen medication, and quantitative comparison of the short term effects of combinations of medications.

In one embodiment of the invention, a method involves administering a nitrate-type medication to a patient in small, increasing doses, while one or more various hemodynamic parameters and performance ratios are monitored. Measured parameters may then be plotted on one axis of a graph, while the dose concentration of the medication is plotted on the opposing axis. For example, Cardiac Reserve (CR) (y-axis) as a function of nitrate dose (x-axis) may be plotted. A three dimensional plot may be used to express, for example, Cardiac Reserve (z-axis) against LVEDP (x-axis) and Nitrate Dose (y-axis), where the x, y, and z axes are isometrically presented as if a corner of a cube.

In a further example, a new "set point," or optimal hemodynamic parameter set for a patient, may be produced by some combination of medications at concentration levels determined during the catheterization. (For example, the LVEDP may be lowered to some value, the cardiac output may be increased to some value, and the SVR may be lowered to some value, each of which is expected to have a therapeutic benefit.) The patient could then be given a "prescription" using similar-acting oral medications to maintain that set point long after the catheterization has ended.

In a further example, the catheter may be placed in the aorta, where the stiffness and compliance of the aorta may be directly measured. This type of measurement might be used before and after a drug treatment (for example, EDTA may be infused into the femoral vein) to test the effectiveness of that medication in increasing aortic compliance. Similarly, the catheter may be placed in the left ventricle and the patient given an inotropic agent whose purpose is to modify the compliance of the ventricle. Without changing the end diastolic pressure, the effect of the medication on ventricular compliance as a function of dosing levels may be directly measured, recorded and displayed.

Although the foregoing description is a complete and accurate description of the invention, it is offered for exemplary purposes only and should not be interpreted to limit the scope of the present invention as it is defined in the claims. Various changes, additions, substitutions, and/or the like may be made to many of the methods, devices, and systems described above, without departing from the scope of the invention as claimed. For example, in some embodiments one or more pharmalogical classes such as inotropic agents, phosphodiesterase inhibitors, Beta and calcium channel blockers, diuretics, afterload reduction agents, cardiac glycosides and neurohormonal agents may be administered and various hemodynamic parameters may be measured. Such methods may be performed at rest or with exercise, with or without alterations in cardiac electrical stimulation, as with a pacemaker or biventricular pacing device. Many other embodiments and variations are contemplated within the scope of the invention.

What is claimed is:

1. A method for measuring a cardiac performance parameter, the method comprising repeating over a series of two or more consecutive heart cycles:
    causing a change in at least one of volume and pressure in a heart chamber at a selected time during a heart cycle;
    measuring a change in at least one characteristic of the heart chamber which occurs in response to the change in at least one of volume and pressure; and
    calculating at least one cardiac performance parameter based on a ratio of the measured change in the characteristic to the caused change.

2. A method as in claim 1, wherein causing the change comprises introducing a volume of fluid into the heart chamber during diastole.

3. A method as in claim 2, wherein introducing the volume of fluid comprises releasing the fluid within the heart chamber via one or more apertures in a catheter positioned in the chamber.

4. A method as in claim 2, wherein introducing the volume of fluid comprises inflating an expandable balloon coupled with a catheter positioned in the heart chamber.

5. A method as in claim 4, wherein inflating the balloon comprises: inflating the balloon during systole of the heart; and deflating the balloon during diastole of the heart immediately following the systole.

6. A method as in claim 4, wherein inflating the balloon comprises: inflate the balloon during diastole of the head; and deflating the balloon during systole of the heart immediately following the diastole.

7. A method as in claim 2, wherein introducing the volume of fluid comprises: inflating a balloon within the heart chamber during systole; deflating the balloon during diastole immediately following the systole; and releasing an amount of fluid within the heart chamber during the diastole.

8. A method as in claim 7, wherein the balloon is deflated by a volume equal to the amount of the released fluid.

9. A method as in claim 7, wherein the balloon is deflated by a volume greater than the amount of the released fluid.

10. A method as in claim 1, wherein causing the change comprises activating a hydrophone at least once during diastole.

11. A method as in claim 10, wherein activating comprises activating the hydrophone at a frequency of about 200 Hz.

12. A method as in claim 10, wherein activating comprises activating the hydrophone at a frequency of about 500 Hz.

13. A method as in claim 10, wherein activating comprises activating the hydrophone at a frequency of about 1000 Hz.

14. A method as in claim 1, wherein causing the change comprises inducing a paroxysmal ventricular contraction.

15. A method as in claim 14, wherein the paroxysmal ventricular contraction is induced by electrical stimulation.

16. A method as in claim 1, further comprising measuring the heart cycle using an electrocardiogram device, wherein the selected time during the heart cycle is selected using the electrocardiogram measurement.

17. A method as in claim 1, further comprising measuring the heart cycle using at least one sensor on a catheter positioned in the heart chamber, wherein the selected time during the heart cycle is selected using the sensor measurement.

18. A method as in claim 1, wherein the change in the cardiac characteristic is measured immediately after causing a change in at least one of volume and pressure.

19. A method as in claim 1, wherein the change in the cardiac characteristic is measured during at least a portion of the heart cycle after the change in at least one of the volume and pressure.

20. A method as in claim 1, wherein measuring the change comprises measuring a change in at least one pressure within the heart chamber.

21. A method as in claim 20, wherein measuring the change in pressure comprises measuring a change in end-diastolic pressure and a change in end-systolic pressure.

22. A method as in claim 21, wherein calculating the at least one parameter comprises calculating a cardiac pressure gain, comprising: calculating a first difference between a first end-systolic pressure and a second end-systolic pressure; calculating a second difference between a first end-diastolic pressure and a second end-diastolic pressure; and dividing the first difference by the second difference.

23. A method as in claim 22, further comprising providing at least one of the end-diastolic pressures, the end-systolic pressures and the cardiac pressure gain for display on a display device.

24. A method as in claim 23, wherein the providing step comprises providing data in the form of a plot, with at least one end-diastolic pressure on one axis of the plot and at least one end-systolic pressure on a perpendicular axis of the plot.

25. A method as in claim 20, wherein measuring the change comprises measuring a change in left ventricular end-diastolic pressure and a change in left ventricular end-systolic pressure.

26. A method as in claim 1, wherein measuring the change comprises measuring a change in at least one volume within the heart chamber.

27. A method as in claim 26, wherein measuring the change comprises measuring a change in end-diastolic volume and a change in end-systolic volume.

28. A method as in claim 27, wherein calculating the at least one parameter comprises calculating a volume reserve comprising: calculating a first difference between a first end-systolic volume and a second end-systolic volume; calculating a second difference between a first end-diastolic volume and a second end-diastolic volume; and dividing the first difference by the second difference.

29. A method as in claim 28, further comprising providing at least one of the end-diastolic volumes, the end-systolic volumes and the volume reserve for display on a display device.

30. A method as in claim 29, wherein the providing step comprises providing data in the form of a plot, with at least one end-diastolic volume on one axis of the plot and at least one end-systolic volume on a perpendicular axis of the plot.

31. A method as in claim 27, wherein measuring the change comprises measuring a change in a left ventricular end-diastolic volume and a change in a left ventricular end-systolic volume.

32. A method as in claim 1, wherein measuring the change comprises measuring a change in at least one pressure and a change in at least one volume within the heart chamber.

33. A method as in claim 32, wherein measuring the change comprises measuring a change in end-diastolic volume and a change in end-diastolic pressure.

34. A method as in claim 33, further comprising providing pressure and volume data as a plot, with at least one volume on one axis of the plot and at least one volume on a perpendicular axis of the plot.

35. A method as in claim 33, wherein calculating the at least one parameter comprises calculating a lusitropic stiffness of the heart chamber, comprising: calculating a first difference between a second end-diastolic pressure and a first end-diastolic pressure; calculating a second difference between a second end-diastolic volume and a first end-diastolic volume; and dividing the first difference by the second difference.

36. A method as in claim 35, further comprising providing at least one of the volumes, the pressures and the lusitropic stiffness for display on a display device.

37. A method as in claim 33, wherein calculating the at least one parameter comprises calculating a lusitropic compliance of the head chamber, comprising: calculating a first difference between a second end-diastolic volume and a first end-diastolic volume; calculating a second difference between a second end-diastolic pressure and a first end-diastolic pressure; and dividing the first difference by the second difference.

38. A method as in claim 37, further comprising providing at least one of the volumes, the pressures and the lusitropic compliance for display on a display device.

39. A method as in claim 32, wherein measuring the change comprises measuring a change in end-systolic volume and a change in end-systolic pressure.

40. A method as in claim 39, further comprising providing volume and pressure data as a plot, with at least one volume on one axis of the plot and at least one volume on a perpendicular axis of the plot.

41. A method as in claim 39, wherein calculating the at least one parameter comprises calculating an inotropic stiffness of the head chamber, comprising; calculating a first difference between a second end-systolic pressure and a first end-systolic pressure; calculating a second difference between a second end-systolic volume and a first end-systolic volume; and dividing the first difference by the second difference.

42. A method as in claim 41, further comprising providing at least one of the volumes, the pressures and the inotropic stiffness for display on a display device.

43. A method as in claim 39, wherein calculating the at least one parameter comprises calculating an inotropic compliance of the head chamber, comprising: calculating a first difference between a second end-systolic volume and a first end-systolic volume; calculating a second difference between a second end-systolic pressure and a first end-systolic pressure; and dividing the first difference by the second difference.

44. A method as in claim 43, further comprising providing at least one of the volumes, the pressures and the inotropic compliance for display on a display device.

45. A method as in claim 32, wherein the measuring and calculating steps comprise: continuously measuring a pressure and volume in the heart chamber during a heart cycle; calculating a first integral of the pressure as a function of volume as the volume increases due to expansion of the ventricle; calculating a second integral of the pressure as a function of volume as the volume decreases due to contraction of the ventricle; and calculating a myocardial work of the heart chamber by subtracting the second integral from the first integral.

46. A method as in claim 32, wherein the measuring and calculating steps comprise: continuously measuring a pressure and volume in the heart chamber during a heart cycle; calculating a first integral of the product of the pressure and the volume as the volume increases due to expansion of the ventricle; calculating a second integral of the product of the pressure and the volume as the volume decreases due to contraction of the ventricle; and calculating a first moment of myocardial work of the heart chamber by subtracting the second integral from the first integral.

47. A method as in claim 45, further comprising: calculating a body surface are; and calculating a myocardial work index by dividing the myocardial work by the body surface area.

48. A method as in claim 45, further comprising: calculating a stroke ejection period by calculating the time when the velocity in the aorta begins to increase from zero to the time when the velocity in the aorta first returns to zero; and calculating a myocardial power by dividing the myocardial work by the stroke ejection period.

49. A method as in claim 48, further comprising calculating a body surface area; and calculating a myocardial power index by dividing myocardial power by body surface area.

50. A method as in claim 48, further comprising calculating a stroke volume; and calculating a myocardial power requirement parameter by dividing myocardial power by stroke volume.

51. A method as in claim 45, further comprising: calculating a first myocardial work for the first heart cycle; changing the end-diastolic volume and pressure; calculating a second myocardial work for a second heart cycle; measuring a first end-diastolic pressure for the first heart cycle and a second end-diastolic pressure for the second heart cycle; and calculating a myocardial reserve by dividing a difference between the second and first myocardial works by a difference between the second and the first end-diastolic pressures.

52. A method as in claim 51, further comprising: calculating a body surface area; and calculating a myocardial reserve index by dividing the myocardial reserve by the body surface area.

53. A method as in claim 45, wherein the myocardial work is calculated for a left ventricle of a heart.

54. A method as in claim 45, wherein the myocardial work is calculated for a right ventricle of a heart.

55. A method as in claim 45, further comprising: calculating a first myocardial power for the first heart cycle; changing the end-diastolic volume and pressure; calculating a second myocardial power for a second heart cycle; measuring a first end-diastolic pressure for the first heart cycle and a second end-diastolic pressure for the second heart cycle; and calculating a myocardial power reserve by dividing a difference between the second and first myocardial powers by a difference between the second and the first end-diastolic pressures.

56. A method as in claim 55, further comprising: calculating a body surface area; and calculating a myocardial power reserve index by dividing the myocardial power reserve by the body surface area.

57. A method as in claim 1, further comprising: measuring a change in at least one flow rate of blood flowing out of the heart chamber which occurs in response to the volume and/or pressure change; and calculating at least one flow-related parameter of the heart chamber based on a ratio of the measured change in the flow rate to the volume and/or pressure change.

58. A method as in claim 57, wherein measuring the change in the flow rate comprises measuring at least one flow rate in an aorta.

59. A method as in claim 57, wherein measuring the change in the flow rate comprises measuring at least one flow rate in at least one pulmonary artery.

60. A method as in claim 57, wherein calculating the flow-related parameter comprises calculating at least one stroke volume of a heart from which the flow rate is measured, the method further comprising: estimating a cardiac output for the heart; measuring a rate of the heart; calculating a first ratio by dividing the estimated cardiac output by the heart rate; calculating a first integral of the flow rate over a number of heart cycles; calculating a second ratio by dividing the integral by the number of heart cycles; calculating a scaling factor by dividing the first ratio by the second ratio; calculating a second integral of the flow rate over a selected heart cycle; and calculating the stroke volume by multiplying the second integral by the scaling factor.

61. A method as in claim 60, further comprising: measuring a body surface area; and calculating a stroke volume index by dividing the stroke volume by the body surface area.

62. A method as in claim 60, wherein the cardiac output is estimated using at least one of Fick's method and a dilution method.

63. A method as in claim 60, further comprising determining a calculated cardiac output by dividing the stroke volume by a time of duration of one of the heart cycles.

64. A method as in claim 63, further comprising: measuring a body surface area; and calculating a cardiac index by dividing the calculated cardiac output by the body surface area.

65. A method as in claim 63, further comprising: determining a first calculated cardiac output and a second calculated cardiac output for first and second heart cycles; measuring first end-diastolic pressure and a second end-diastolic pressure for the first and second head cycles; and calculating a cardiac reserve by dividing a difference between the second and first calculated cardiac outputs by a difference between the second and first end-diastolic pressures.

66. A method as in claim 65, further comprising: measuring a body surface area; and calculating a cardiac reserve index by dividing the calculated cardiac reserve by the body surface area.

67. A method as in claim 60, further comprising: calculating a first stroke volume and a second stroke volume for first and second cardiac cycles; measuring first end-diastolic pressure and a second end-diastolic pressure for the first and second heart cycles; and calculating a stroke reserve by dividing a difference between the second and first calculated stroke volumes by a difference between the second and first end-diastolic pressures.

68. A method as in claim 67, further comprising: measuring a body surface area; and calculating a stroke reserve index by dividing the calculated stroke reserve by the body surface area.

69. A method as in claim 60, further comprising: measuring an average systolic pressure in at least one outflow artery adjacent the heart; measuring an average diastolic pressure in the heart chamber; calculating a difference between the average systolic pressure and the average diastolic pressure; and calculating a stroke work by multiplying the difference by the stroke volume.

70. A method as in claim 69, further comprising: measuring a body surface area; and calculating a stroke work index by dividing the calculated stroke work by the body surface area.

71. A method as in claim 69, further comprising: calculating a first stroke work and a second stroke work for first and second cardiac cycles; measuring first end-diastolic pressure and a second end-diastolic pressure for the first and second heart cycles; and calculating a stroke work reserve by dividing a difference between the second and first calculated stroke works by a difference between the second and first end-diastolic pressures.

72. A method as in claim 71, further comprising: measuring a body surface area; and calculating a stroke work reserve index by dividing the calculated stroke work reserve by the body surface area.

73. A method as in claim 69, wherein the at least one outflow artery comprises an aorta.

74. A method as in claim 69, wherein the at least one outflow artery comprises at least one pulmonary artery.

75. A method as in claims 45 and 69, further comprising calculating a cardiac efficiency by dividing the stroke work by the myocardial work.

76. A method as in claim 60, further comprising: calculating a first stroke volume and a second stroke volume for first and second cardiac cycles; measuring first end-diastolic volume and a second end-diastolic volume for the first and second heart cycles; and calculating a cardiac amplification by dividing a difference between the second and first calculated stroke volumes by a difference between the second and first end-diastolic volumes.

77. A method as in claim 60, further comprising calculating a first difference between a second product of volume and pressure and a first product of volume and pressure, said second volume and pressure measured shortly after the first; calculating a determination of the incremental stroke volume which is the product of the scaling factor and the integral of the velocity in the proximal artery between the first and second times; calculating the period of time between the first measurement and the second; calculating a third product between the incremental stroke volume and the period of time; and calculating an ejection contractility parameter by dividing the first difference by the third product.

* * * * *

UNITED STATES PATENT AND TRADEMARK OFFICE
CERTIFICATE OF CORRECTION

| | | |
|---|---|---|
| PATENT NO. | : 7,204,798 B2 | Page 1 of 1 |
| APPLICATION NO. | : 10/764127 | |
| DATED | : April 17, 2007 | |
| INVENTOR(S) | : Mark J. Zdeblick et al. | |

It is certified that error appears in the above-identified patent and that said Letters Patent is hereby corrected as shown below:

In the Specification:

In column 15-16 table 1: Delete "performe" and replace with --performed--.
In column 15-16 table 1: Insert --in-- before the phrase "LVEDP".
In column 17-18 table 1: Delete "ressure" and replace with --pressure--.
In column 17-18 table 1: Delete "Regurgitatio" and replace with --Regurgitation--.

In The Claims:

Claim 6 line 13: Delete "head" and replace it with --heart--.
Claim 37 line 62: Delete "head" and replace it with --heart--.
Claim 41 line 13: Insert --head-- before the phrase "heart".
Claim 43 line 24: Delete "head" and replace it with --heart--.
Claim 65 line 15: Delete "head" and replace it with --heart--.

Signed and Sealed this

Eighteenth Day of December, 2007

JON W. DUDAS
*Director of the United States Patent and Trademark Office*